US010034922B2

(12) United States Patent
Kim

(10) Patent No.: US 10,034,922 B2
(45) Date of Patent: Jul. 31, 2018

(54) PEPTIDE HAVING ANGIOGENESIS INHIBITORY ACTIVITY AND COMPOSITION CONTAINING SAME

(71) Applicant: GemVax & KAEL Co., Ltd., Daejeon (KR)

(72) Inventor: Sang Jae Kim, Seoul (KR)

(73) Assignee: GemVax & KAEL Co., Ltd., Dejeon (KR)

( * ) Notice: Subject to any disclaimer, the term of this patent is extended or adjusted under 35 U.S.C. 154(b) by 0 days.

(21) Appl. No.: 15/038,269

(22) PCT Filed: Nov. 21, 2014

(86) PCT No.: PCT/KR2014/011280
§ 371 (c)(1),
(2) Date: May 20, 2016

(87) PCT Pub. No.: WO2015/076621
PCT Pub. Date: May 28, 2015

(65) Prior Publication Data
US 2016/0296604 A1    Oct. 13, 2016

(30) Foreign Application Priority Data

Nov. 22, 2013 (KR) .................. 10-2013-0142897
Feb. 21, 2014 (KR) .................. 10-2014-0020605

(51) Int. Cl.
| A61K 38/00 | (2006.01) |
| A61K 38/45 | (2006.01) |
| C12N 9/12 | (2006.01) |
| A23L 33/17 | (2016.01) |

(52) U.S. Cl.
CPC .............. *A61K 38/45* (2013.01); *A23L 33/17* (2016.08); *C12N 9/1276* (2013.01); *C12Y 207/07049* (2013.01); *A23V 2002/00* (2013.01); *A61K 38/00* (2013.01)

(58) Field of Classification Search
CPC ...... A61K 38/00; A61K 38/45; C12N 9/1276; C12Y 207/07049
USPC ................................. 514/21.4, 13.3
See application file for complete search history.

(56) References Cited

U.S. PATENT DOCUMENTS

| 6,967,211 B2 | 11/2005 | Inoue |
| 7,030,211 B1 | 4/2006 | Gaudernack et al. |
| 7,786,084 B2 | 8/2010 | Benner et al. |
| 7,794,723 B2 | 9/2010 | Gaudernack et al. |
| 8,828,403 B2 | 9/2014 | Filaci et al. |
| 8,933,197 B2 | 1/2015 | Bogin et al. |
| 9,023,987 B2 | 5/2015 | Chung et al. |
| 9,540,419 B2 | 1/2017 | Kim et al. |
| 9,572,858 B2 | 2/2017 | Kim |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1 | 5/2006 | Gaudernack et al. |
| 2007/0190561 A1 | 8/2007 | Morin et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0065124 A1 | 3/2012 | Morishita et al. |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim |
| 2015/0307859 A1 | 10/2015 | Kim |
| 2015/0343095 A1 | 12/2015 | Kim |
| 2015/0353903 A1 | 12/2015 | Kim |
| 2016/0002613 A1 | 1/2016 | Kim |
| 2016/0008438 A1 | 1/2016 | Kim |
| 2016/0082089 A1 | 3/2016 | Kim |
| 2016/0120966 A1 | 5/2016 | Kim |
| 2016/0137695 A1 | 5/2016 | Kim |
| 2016/0151512 A1 | 6/2016 | Sang |
| 2016/0250279 A1 | 9/2016 | Kim |
| 2016/0375091 A1 | 12/2016 | Kim |
| 2017/0028035 A1 | 2/2017 | Kim |
| 2017/0058001 A1 | 3/2017 | Kim |
| 2017/0081376 A1 | 3/2017 | Kim et al. |

(Continued)

FOREIGN PATENT DOCUMENTS

| EP | 1020190 A3 | 10/2000 |
| EP | 1093381 B2 | 7/2009 |

(Continued)

OTHER PUBLICATIONS

Auerbach et al., "Angiogenesis assays: Problems and pitfalls," Cancer and Metastasis Reviews, 2000, 19: 167-172.*
Jain RK, "Barriers to Drug Delivery in Solid Tumors," Scientific American, 1994, 58-65.*
Albini et al, "Cancer prevnetion by targeting angiogenesis," Nature, 2012, 1-12.*
Eisenegger, C., et al., "The Role of Testosterone in Social Interaction," Trends in Cognitive Sciences 15(6):263-271, Elsevier Ltd., England (2011).
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (Sep. 2013).

(Continued)

*Primary Examiner* — Julie Ha
(74) *Attorney, Agent, or Firm* — Sterne, Kessler, Goldstein & Fox P.L.L.C.

(57) ABSTRACT

A peptide having angiogenesis inhibition activity and pharmaceutical composition comprising thereof is described. More specifically, the application relates to the pharmaceutical composition for inhibiting angiogenesis comprising the peptide as a peptide derived from telomerase.

16 Claims, 35 Drawing Sheets

(56) References Cited

U.S. PATENT DOCUMENTS

| | | |
|---|---|---|
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 9/2017 | Kim et al. |

FOREIGN PATENT DOCUMENTS

| | | |
|---|---|---|
| EP | 1817337 B1 | 1/2011 |
| JP | 2002522373 A | 7/2002 |
| JP | 2010252810 A | 11/2010 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060065588 A | 6/2006 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130996 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| WO | WO-0002581 A1 | 1/2000 |
| WO | WO-2010003520 A2 | 1/2010 |
| WO | WO-2010012850 A1 | 2/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015093854 A1 | 6/2015 |
| WO | WO-2015156649 A1 | 10/2015 |
| WO | WO-2015167067 A1 | 11/2015 |
| WO | WO-2016105086 A1 | 6/2016 |
| WO | WO-2016137162 A1 | 9/2016 |

OTHER PUBLICATIONS

Guo, R.-F., et al., "Regulatory Effects of Eotaxin on Acute Lung Inflammatory Injury," Journal of Immunology 166(8):5208-5218, The American Association of Immunologists, United States (2001).

Heldin, C.-H., et al., "TGF-β Signalling from Cell Membrane to Nucleus through SMAD Proteins," Nature 390(6659):465-471, Nature Publishing Group, England (1997).

International Preliminary Report on Patentability for International Application No. PCT/KR2014/004752, The International Bureau of WIPO, Switzerland, dated Nov. 1, 2016, 23 pages.

International Preliminary Report on Patentability for International Application No. PCT/KR2015/003642, The International Bureau of WIPO, Switzerland, dated Oct. 12, 2016, 18 pages.

International Preliminary Report on Patentability for International Application No. PCT/KR2014/010035, Korean Intellectual Property Office, Republic of Korea, dated Apr. 26, 2016, 13 pages.

International Search Report for International Application No. PCT/KR2014/004752, Korean Intellectual Property Office, Republic of Korea, dated Jan. 16, 2015, 10 pages.

International Search Report for International Application No. PCT/KR2015/003642, Korean Intellectual Property Office, Republic of Korea, dated Jul. 3, 2015, 8 pages.

JoongAng Ilbo, "Seoul National University Bundang Hospital excited because of '000', Clinical trials of Dream Anticancer Drug without side effects with Kael & GemVax," published Apr. 22, 2013, accessed at http://news.joins.com/article/print/11297202, accessed on Dec. 22, 2015, 4 pages.

Kawasaki, H., et al., "Detection and Evaluation of Activation of Various Cancer Antigenic Peptide-specific CTLs in Mature Dendritic Cells Used for Dendritic Cell Therapy," The 21st International Congress of Personalized Medicine, Conference Program and Abstracts, Personalized Medicine Universe (Japanese edition) 4(Supplement 2):66, published Oct. 17, 2015, 5 pages.

Kyte, J.A., et al., "Telomerase Peptide Vaccination Combined with Temozolomide: A Clinical Trial in Stage IV Melanoma Patients," Clinical Cancer Research 17(13):4568-4580, The American Association of Cancer Research, United States (2011).

Massagué, J., "TGF-β Signal Transduction," Annual Review of Biochemistry 67:753-791, Annual Reviews, United States (1998).

Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet Oncology 15(8):829-840, Lancet Publishing Group, England (Jul. 2014).

Morishita, M. and Peppas, N.A., "Is the Oral Route Possible for Peptide and Protein Drug Delivery?," Drug Discovery Today 11(19-20):905-910, Elsevier Ltd., England (2006).

National Institute of Diabetes and Digestive and Kidney Diseases, "Prostate Enlargement: Benign Prostatic Hyperplasia," accessed at https://www.niddk.nih.gov/health-information/urologic-diseases/prostate-problems/prostate-enlargement-benign-prostatic-hyperplasia, updated Sep. 2014, 14 pages.

National Institutes of Health, "Adjuvant Leuprolide With or Without Docetaxel in High Risk Prostate Cancer After Radical Prostatectomy," ClinicalTrials.gov Identifier NCT00283062, clinicaltrials.gov, accessed at https://clinicaltrials.gov/ct2/show/study/NCT00283062, accessed on May 12, 2017, 7 pages.

National Institutes of Health, "Gemcitabine and Capecitabine With or Without Vaccine Therapy in Treating Patients With Locally Advanced or Metastatic Pancreatic Cancer," ClinicalTrials.gov Identifier NCT00425360, clinicaltrials.gov, accessed at https://clinicaltrials.gov/archive/NCT00425360/2007_01_22, accessed on Apr. 7, 2017, 4 pages.

National Library of Medicine, National Center for Biotechnology Information, MeSH Database, "Hormones," accessed at http://www.ncbi.nlm.nih.gov/mesh/68006728, accessed on May 8, 2017, 3 pages.

Sasada, A., et al., "A Case of Elderly Patient With Lung Cancer Efficiently Treated With Dendritic Cell Immunotherapy" The 20th International Congress of Personalized Medicine, Conference Program and Abstracts, Personalized Medicine Universe (Japanese edition) 4(Supplement 1):50, published May 24, 2015, 2 pages.

Shaw, V.E., et al., "Current Status of GV1001 and Other Telomerase Vaccination Strategies in the Treatment of Cancer," Expert Review of Vaccines 9(9):1007-1016, Taylor & Francis, England (2010).

Song, J., et al., "Characterization and Fate of Telomerase-Expressing Epithelia during Kidney Repair," Journal of the American

(56) References Cited

OTHER PUBLICATIONS

Society of Nephrology 22(12):2256-2265, American Society of Nephrology, United States (2011).
Wang, W., et al., "Alleviating the Ischemia-Reperfusion Injury of Donor Liver by Transfection of Exogenous hTERT Genes," Transplantation Proceedings 41(5):1499-1503, Elsevier Inc., United States (2009).
Written Opinion for International Application No. PCT/KR2014/004752, Korean Intellectual Property Office, Republic of Korea, dated Jan. 16, 2015, 21 pages.
Written Opinion for International Application No. PCT/KR2014/010035, Korean Intellectual Property Office, Republic of Korea, dated Feb. 2, 2015, 11 pages.
Written Opinion for International Application No. PCT/KR2015/003642, Korean Intellectual Property Office, Republic of Korea, dated Jul. 3, 2015, 16 pages.
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (Jul. 2013).
Altschul, S.F., et al., "Basic Local Alignment Search Tool," Journal of Molecular Biology 215(3):403-410, Elsevier, England (1990).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Brandenburg, K., et al., "Peptide-based Treatment of Sepsis," Applied Microbiology and Biotechnology 90(3):799-808, Springer International, Germany (2011).
Bruns, A.F., et al., "A Heat-shock Protein Axis Regulates VEGFR2 Proteolysis, Blood Vessel Development and Repair," PloS One 7(11):e48539, Public Library of Science, United States (2012).
Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).
Calderwood, S.K., et al., "Heat Shock Proteins in Cancer: Chaperones of Tumorigenesis," Trends in Biochemical Sciences 31(3):164-172, Elsevier Trends Journals, England (2006).
Cho, Y.J., "GemVax & Kael (082270)," Hana Daetoo Securities, Company Report, Sep. 10, 2012, 8 pages.
Choi, S.G., "Recent Advances in Cancer Cachexia," Journal of Korean Oncology Nursing 11(1):20-25 (2011).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
Dementia from Merck Manual, accessed on Jul. 29, 2009, pp. 1-17.
Dempsey, N.C., et al., "Differential Heat Shock Protein Localization in Chronic Lymphocytic Leukemia," Journal of Leukocyte Biology 87(3):467-476, Society for Leukocyte Biology, United States (2010).
Dinarello, C.A., "Interleukin-1 in the Pathogenesis and Treatment of Inflammatory Diseases," Blood 117(14):3720-3732, American Society of Hematology, United States (2011).
Du, R., et al., "HIF1 alpha Induces the Recruitment of Bone Marrow-derived Vascular Modulatory Cells to Regulate Tumor Angiogenesis and Invasion," Cancer Cell 13(3):206-220, Cell Press, United States (2008).
Engineer, D.R. and Garcia, J.M., "Leptin in Anorexia and Cachexia Syndrome," International Journal of Peptides 2012:Article ID 287457, Hindawi Publishing Corporation, United States (2012).
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Ferrarini, M., et al., "Unusual Expression and Localization of Heat-shock Proteins in Human Tumor Cells," International Journal of Cancer51(4):613-619, Wiley-Liss, United States (1992).
Fire, A., et al., "Potent and Specific Genetic Interference by Double-stranded RNA in Caenorhabditis elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
Garcia-Carbonero, R., et al., "Inhibition of HSP90 Molecular Chaperones: Moving Into the Clinic," The Lancet Oncology 14(9):e358-e369, Lancet Publishing Group, England (2013).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Heitz, F., et al., "Twenty Years of Cell-Penetrating Peptides: From Molecular Mechanisms to Therapeutics," British Journal of Pharmacology 157(2):195-206, Wiley, England (2009).
HSE, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).
International Preliminary Report on Patentability for International Application No. PCT/KR2014/011280, The International Bureau of WIPO, Geneva, Switzerland, dated May 24, 2016, 15 pages.
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014,14 pages.
International Preliminary Report on Patentability for International Application No. PCT/KR2013/004176, The International Bureau of WIPO, Switzerland, dated Nov. 11, 2014,14pages.
International Preliminary Report on Patentability for International Application No. PCT/KR2013/006218, The International Bureau of WIPO, Switzerland, dated Jan. 13, 2015,27 pages.

(56) References Cited

OTHER PUBLICATIONS

International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/KR2014/011280, Korean Intellectual Property Office, Republic of Korea, dated Feb. 11, 2015, 12 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Patent Application No. PCT/KR2013/004156, Korean Intellectual Property Office, Republic of Korea, dated Aug. 14, 2013, 10 pages.
International Search Report for International Application No. PCT/KR2013/008459, Korean Intellectual Property Office, Republic of Korea, dated Dec. 23, 2013, 8 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Kern, K.A. and Norton, J.A., "Cancer Cachexia," Journal of Parenteral and Enteral Nutrition 12(3):286-298, Sage Publications, United States (1988).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).

Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).
Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Morano, K.A., "New Tricks for an Old Dog: The Evolving World of Hsp70," Annals of the New York Academy of Sciences 1113:1-14, Blackwell, United States (2007).
Murphy, M.E., "The Hsp70 Family and Cancer," Carcinogenesis 34(6):1181-1188, Irl Press, England (2013).
Myers, L.K., et al., "Collagen-Induced Arthritis, an Animal Model of Autoimmunity," Life Sciences 61(19):1861-1878, Elsevier, Netherlands (1997).
Nagaraju, G.P., et al., "Antiangiogenic Effects of Ganetespib in Colorectal Cancer Mediated Through Inhibition of HIF-1αand STAT-3," Angiogenesis 16(4):903-917, Springer, Germany (2013).
National Horizon Scanning Centre News on Emerging Technologies in Healthcare, GV1001 for Advanced and/or Metastatic Pancreatic Cancer, Published Apr. 2008.
NCBI, Reference Sequence: XP_003776612.1 (Jul. 17, 2012).
Novina, C.D. and Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences 98(18): 10308-10313, National Academy of Sciences, United States (2001).

(56) References Cited

OTHER PUBLICATIONS

Pearson, W.R. and Lipman, D.J., "Improved Tools for Biological Sequence Comparison," Proceedings of the National Academy of Sciences USA 85(8):2444-2448, National Academy of Sciences, United States (1988).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Rana, T.M., "Illuminating the Silence: Understanding the Structure and Function of Small RNAs," Nature Reviews. Molecular Cell Biology 8(1):23-36, Nature Publishing Group, England (2007).
Rheumatoid Arthritis from Merck Manual, accessed on Apr. 21, 2016, pp. 1-18.
Roubenoff, R., et al., "Adjuvant Arthritis as a Model of Inflammatory Cachexia," Arthritis and Rheumatism 40(3):534-539, Wiley-Blackwell, United States (1997).
Schenk, D., et al., "Immunization with Amyloid-beta Attenuates Alzheimer-disease-like Pathology in the PDAPP Mouse," Nature 400(6740):173-177, Nature Publishing Group, England (1999).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Seo, J.S., et al., "T Cell Lymphoma in Transgenic Mice Expressing the Human Hsp70 Gene," Biochemical and Biophysical Research Communications 218(2):582-587, Elsevier, United States (1996).
Shay, J.W., and Wright, W.E., "Telomerase Therapeutics for Cancer: Challenges and New Directions," Nature Reviews. Drug Discovery 5(7):577-584, Nature Publishing Group, England (2006).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).
Smith, T.F. and Waterman, M.S., "Comparison of Biosequences," Advances in Applied Mathematics 2(4):482-489, Academic Press, Inc., United States (1981).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw /1/itemID/124/Rheumatoid-arthritis-causes-symptoms-treatment.aspx, last reviewed on May 31, 2013, 5 pages.
Stevenson, C.L., "Advances in Peptide Pharmaceuticals," Current Pharmaceutical Biotechnology 10(1):122-137, Bentham Science Publishers, United Arab Emirates (2009).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).
Tisdale, M.J., "Mechanisms of Cancer Cachexia," Physiological Reviews 89(2):381-410, American Physiological Society, United States (2009).

Tomari Y. and Zamore, P.D., "Perspective: Machines for RNAi," Genes and Development 19(5):517-529, Cold Spring Harbor Laboratory Press, United States (2005).
Uehara, Y., "Natural Product Origins of Hsp90 Inhibitors," Current Cancer Drug Targets 3(5):325-330, Bentham Science Publishers, Netherlands (2003).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Vennela, B., et al., "Current and Future Strategies for Therapy of Pancreatic Cancer," International Journal of Research in Pharmacy and Medicine 2(3):728-740 (2012).
Volloch, V.Z. and Sherman, M.Y., "Oncogenic Potential of Hsp72," Oncogene 18(24):3648-3651, Nature Publishing Group, England (1999).
Walsmith, J. and Roubenoff, R., "Cachexia in Rheumatoid Arthritis," International Journal of Cardiology 85(1):89-99, Elsevier, Netherlands (2002).
Written Opinion for International Application No. PCT/KR2014/011280, Korean Intellectual Property Office, Republic of Korea, dated Feb. 11, 2015, 14 pages.
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2013/008459, Korean Intellectual Property Office, Republic of Korea, dated Dec. 23, 2013, 9 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Yeh, C.H., et al., "Clinical Correlation of Circulating Heat Shock Protein 70 in Acute Leukemia," Leukemia Research 34(5):605-609, Pergamon Press, England (2010).
Zhou, J., et al., "PI3K/Akt Is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).

(56) References Cited

OTHER PUBLICATIONS

Beer, T.M., et al., "Phase II Study of Weekly Docetaxel in Symptomatic Androgen-independent Prostate Cancer," Annals of Oncology 12(9):1273-1279, Oxford University Press, England (2001).
Henry, J.Y., et al., "Lenalidomide Enhances the Anti-prostate Cancer Activity of Docetaxel in vitro and in vivo," The Prostate 72(8):856-867, Wiley-Liss, United States (2012).
International Search Report for International Application No. PCT/KR2014/012502, Korean Intellectual Property Office, Republic of Korea, dated Mar. 11, 2015, 10 pages.
International Preliminary Report on Patentability for International Application No. PCT/KR2014/012502, The International Bureau of WIPO, Geneva, Switzerland, dated Jun. 21, 2016, 22 pages.
Jemal, A., et al., "Cancer Statistics, 2008," CA: A Cancer Journal for Clinicians 58(2):71-96, Wiley, United States (2008).
Liu, Q.J., et al., "Rapamycin Enhances the Susceptibility of Both Androgen-dependent and independent Prostate Carcinoma Cells to Docetaxel," Chinese Medical Journal 123(3):356-360, Chinese Medical Association, China (2010).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Written Opinion for International Application No. PCT/KR2014/012502, Korean Intellectual Property Office, Republic of Korea, dated Mar. 11, 2015, 20 pages.
Berendsen, H.J., "A Glimpse of the Holy Grail?," Science 282(5389):642-643, American Association for the Advancement of Science, United States (1998).
De Araujo, J.G., et al., "The Potential Use of Melatonin for Preventing Cisplatin Ototoxicity: An Insight for a Clinical Approach," Advances in Otolaryngology 2014:8 pages, Hindawi Publishing Corporation (2014).
Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.
Du, C., et al., "Conformational and Topological Requirements of Cell-permeable Peptide Function," The Journal of Peptide Research 51(3):235-243, Munksgaard, Denmark (1998).
Extended European Search Report for Application No. EP14808179, dated May 24, 2017, 24 pages.
Fauce, S.R., et al., "Telomerase-Based Pharmacologic Enhancement of Antiviral function of Human CD8+ T Lymphocytes," Immunology 181(10):7400-7406, American Association of Immunologists, United States (Nov. 2008).
Fontanes, V., et al., "A cell permeable peptide inhibits Hepatitis C Virus Replication by Sequestering IRES Transacting Factors, " Virology 394(1):82-90, Academic Press, United States (Nov. 2009).
Fried, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.
International Preliminary Report on Patentability and Written Opinion for International Application No. PCT/KR2015/014099, The International Bureau of WIPO, dated Jun. 27, 2017, 16 pages.
International Preliminary Report on Patentability and Written Opinion for International Application No. PCT/KR2016/001646, Korean Intellectual Property Office, Republic of Korea, dated May 20, 2016, 13 pages.
International Search Report for Application No. PCT/KR2016/007192, dated Sep. 12, 2016, 12 pages.
International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 20, 2016, 8 pages.
Kalnins, A., et al., "Sequence of the Lacz Gene of *Escherichia coli*," The EMBO Journal 2(4):593-597, Wiley Blackwell, England (1983).
Kim, B.H., "Presbycusis: Review for its Environmental Risk Factors," Korean Journal of Otorhinolaryngology-Head and Neck Surgery 49(10):962-967, Korean Society of Otolaryngology-Head and Neck Surgery, Korea (2006).
Kim, H., et al., "Inhibition of HIV-1 Reactivation by a Telomerase-Derived Peptide in a HSP90-Dependent Manner," Scientific Reports 6: 28896, Nature Publishing Group, England (Jul. 2016).
Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015).
Lee, S.A., et al., "A Telomerase-Derived Peptide Regulates Reactive Oxygen Species and Hepatitis C Virus RNA Replication in HCV-Infected Cells Via Heat Shock Protein 90," Biochemical and Biophysical Research Communications 471(1):156-162, Elsevier, United States (Feb. 2016).
Leem G., et al., "Immunotherapy in Pancreatic Cancer; the Road Less Traveled," Immunol Disord Immunotherapy, Jun. 26, 2016 (Jun. 26, 2016), p. 1000106, XP055328627, Retrieved from the Internet: (URL:http://www.omicsgroup.orgjjournalsjimmunotherapy-in-pancreatic-cancer-the-road-less-traveled-IDIT-1000104.pdf).
Mandal, A., "Types of Fibrosis," Retrieved from the internet on Jul. 3, 2014, pp. 1-3.
Merck Manual: Respiratory Diseases, Medical Topics, accessed on Nov. 2, 2017, pp. 1-4.
Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.
Middleton, G.W., "A Phase III 1-20 Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL: http://meetinglibrary.asco.orgjcontent/82894?media=vm).
Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013-Jun. 4, 2013), XP055328310.
Middleton, G.W., et al., Poster: Predictive Cytokine Biomarkers for Survival in Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun. 3, 2014), pp. 1-1. XP055328448. Retrieved from the Internet: (URL:http://media4.asco.org/144/8599/93976/93976_poster_pvhr.jpg).
Nawroth, I., et al., "Intraperitoneal Administration of Chitosan/DsiRNA Nanoparticles Targeting TNFα Prevents Radiation-induced Fibrosis," Radiotherapy and Oncology 97(1):143-148, Elsevier Scientific Publishers, Ireland (2010).
Neoptolemos J.P., et al., "Predictive 1-20 Cytokine Biomarkers for Survival in Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial," 2014 ASCO Annual Meeting, May 30, 2014 (May 30, 2014)-Jun. 3, 2014 (Jun. 3, 2014), pp. 1-3.
Ngo. et al., "Computational Complexity, Protein Structure Prediction, and the Levinthal Paradox," in the Protein Folding Problem and Tertiary Structure Prediction, Merz, Jr., K.M., and Le Grand, S.M., eds., pp. 491-494, Birkhauser Boston, United States (1994).
O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).

(56) References Cited

OTHER PUBLICATIONS

Ortega, V.E., "Asthma," Merck manual, accessed at http://www.merckmanuals.com/professional/pulmonary-disorders/asthma-and-related-disorders/asthma, accessed on Nov. 2, 2017, pp. 1-19.

Priya, S.G., et al., "Skin Tissue Engineering for Tissue Repair and Regeneration," Tissue Engineering. Part B, Reviews 14(1):105-118, Mary Ann Liebert, Inc., United States (2008).

Rosenbloom, J., et al., "Strategies for Anti-fibrotic Therapies," Biochimica et Biophysica Acta 1832(7):1088-1103, Elsevier Pub. Co., Netherlands (2013).

Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.

Rowe-Rendleman, C. and Glickman, R.D., "Possible therapy for age-related macular degeneration using human telomerase," Brain Research Bulletin 62(6):549-553, Elsevier Science Inc., United States (2004).

Rudinger, J., "Characteristics of the Amino Acids as Components of a Peptide Hormone Sequence," in Peptide Hormones, Parsons, J.A., ed., University Park Press, United States (1976).

Schwarze, S.R., et al., "In Vivo Protein Transduction: Delivery of a Biologically Active Protein Into the Mouse," Science 285(5433):1569-1572, American Association for the Advancement of Science, United States (1999).

Sigma Genosys, "Designing Custom Peptides," accessed at http://www.sigma-genosys.com/peptide_design.asp, Accessed on Dec. 16, 2004, 2 pages.

Supplemental European Search Report for Application No. EP14808179, dated Jan. 10, 2017, 13 pages.

Tisdale, M.J., "Catabolic Mediators of Cancer Cachexia," Current Opinion in Supportive and Palliative Care, 2(4):256-261, Lippincott Williams & Wilkins, United States (2008).

Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Apr. 2011).

Voet, D. and Voet, J.G., "Abnormal Hemoglobins," in Biochemistry, 2nd Edition, Chapter 9, pp. 235-241, John Wiley & Sons, Inc., United States (1995).

Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).

Written opinion for Application No. PCT/KR2016/007192, dated Sep. 12, 2016, 16 pages.

Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).

* cited by examiner

SEQUENCE LISTING

```
<160> NUMBER OF SEQ ID NOS: 2

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110
```

-continued

```
Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Arg Arg Val
130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
                195                 200                 205

Glu Ala Gly Val Pro Leu Gly Leu Pro Ala Pro Gly Ala Arg Arg
            210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
275                 280                 285

Leu Ser Gly Thr Arg His Ser His Pro Ser Val Gly Arg Gln His His
            290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
```

```
                530             535             540
Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
                595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
                675                 680                 685

Ala Trp Arg Thr Phe Val Leu Arg Val Arg Ala Gln Asp Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
                755                 760                 765

Leu Gln Pro Tyr Met Arg Gln Phe Val Ala His Leu Gln Glu Thr Ser
                770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
                835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
                915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960
```

-continued

```
Asn Arg Gly Phe Lys Ala Gly Arg Asn Met Arg Arg Lys Leu Phe Gly
                965             970             975

Val Leu Arg Leu Lys Cys His Ser Leu Phe Leu Asp Leu Gln Val Asn
            980             985             990

Ser Leu Gln Thr Val Cys Thr Asn Ile Tyr Lys Ile Leu Leu Leu Gln
        995                 1000            1005

Ala Tyr Arg Phe His Ala Cys Val Leu Gln Leu Pro Phe His Gln
    1010                1015            1020

Gln Val Trp Lys Asn Pro Thr Phe Phe Leu Arg Val Ile Ser Asp
    1025                1030            1035

Thr Ala Ser Leu Cys Tyr Ser Ile Leu Lys Ala Lys Asn Ala Gly
    1040                1045            1050

Met Ser Leu Gly Ala Lys Gly Ala Ala Gly Pro Leu Pro Ser Glu
    1055                1060            1065

Ala Val Gln Trp Leu Cys His Gln Ala Phe Leu Leu Lys Leu Thr
    1070                1075            1080

Arg His Arg Val Thr Tyr Val Pro Leu Leu Gly Ser Leu Arg Thr
    1085                1090            1095

Ala Gln Thr Gln Leu Ser Arg Lys Leu Pro Gly Thr Thr Leu Thr
    1100                1105            1110

Ala Leu Glu Ala Ala Ala Asn Pro Ala Leu Pro Ser Asp Phe Lys
    1115                1120            1125

Thr Ile Leu Asp
    1130
```

PEPTIDE HAVING ANGIOGENESIS INHIBITORY ACTIVITY AND COMPOSITION CONTAINING SAME

BACKGROUND

The proliferation, differentiation and destruction of cells and tissues for maintaining body homeostasis is controlled by a balance of the interactions between various cell-stimulating factors and the cells in the extracellular matrix. When an imbalance occurs in this regulation, various diseases comprising an apoptosis or non-activation to stop signal of proliferation, a nutrition supply by continuous angiogenesis, a malignant tumor expressed by permeation to surrounding tissues and a metastasis occurs.

Angiogenesis comprises all of a degradation of cell basement membrane, a cell movement, an invasion to extra-cell matrix, a cell proliferation, and a synthesis of endothelial cavity of capillary. For inhibition of these, there are a direct method to targeting vascular endothelial cells and an indirect method to targeting cancer cells or surrounding cells which make angiogenesis factors. Studies which aim to develop an anti-body protein to inhibit angiogenesis factor activity or a low molecular material to block the receptor has been largely carried out.

Angiogenesis occurs through a series of steps including a movement and a division of endothelial cells to make blood walls. About 15 kinds of proteins to activate growth and movement endothelial cells are known and they regulate angiogenesis. Therefore, angiogenesis can be inhibited by an inhibitor for inhibiting activation proteins such as angiogenin, epithelial growth factor, estrogen, fibroblast growth factor, interleukin 8, prostaglandin E1 and E2, tumor necrosis factor, or G-CSF (granulocyte colony-stimulating factor).

Heat shock proteins (HSPs) are molecular chaperones which play critical roles in maintaining homeostasis. They are critical for cell survival especially under stresses such as hypoxia. HSPs, especially HSP90 and HSP 70, are highly expressed in a wide range of tumors [Morano K A, Annals of the New York Academy of Sciences, 1113:1-14, 2007; Calderwood S K et al, Trends in biochemical sciences, 31:164-72, 2006]. The expression of several HSPs has been shown to be correlated with tumor cell proliferation, differentiation and apoptosis in several cancers, indicating that HSPs play crucial roles of cancer cell survival due to their cytoprotective role Overexpression of HSP70 induces tumorigenicity to mouse fibrosarcoma cells and overexpression of HSP70 in T-cells of transgenic mice resulted in an increase of T-cell lymphoma in these mice [Jaattela M, International journal of cancer Journal international du cancer, 60:689-93, 1995; Seo J S et al, Biochemical and biophysical research communications, 218:582-7, 1996; Volloch V Z et al, Oncogene, 18:3648-51, 1999; Murphy M E, Carcinogenesis, 34:1181-8, 2013]. Especially, HSP70 has been known to play a crucial role in protecting cells from apoptosis. Besides, overexpression of HSP expression seems to be involved in angiogenesis, invasion, and metastasis [Calderwood S K et al, Trends in biochemical sciences, 31:164-72. 2006; Zhou J et al, The Journal of biological chemistry, 279: 13506-13, 2004; Bruns A F et al, PloS one, 7:e48539, 2012; Sun J et al, Arteriosclerosis, thrombosis and vascular biology. 24:2238-44, 2004; Gong W, et al, Oncology reports, 2013; Eustace B K et al, Cell cycle, 3:1098-100, 2004; Eustace B K et al, Nature cell biology, 6:507-14, 2004].

Based on a theory that cancer can be cured by inhibition of cancer growth and metastasis through blockage of vascularization for supplying oxygen and nutrition to cells, drugs for anti-angiogenesis have been developed for treating not only anti-cancer, but also arthritis, diabetic retinopathy, chronic inflammation, and ischemic heart disease. The treatment of anti-angiogenesis directly inhibits tumor growth and metastasis and indirectly normalize the tumor vascular circumstances to improve effect of treatment which delivers the biological and chemical drugs effectively and refine hypoxia circumstance.

Therefore, there is a need for the development of anti-angiogenesis drugs to treat or prevent malignant tumors, various diseases (arthritis, diabetic retinopathy, chronic inflammation, ischemic heart diseases etc.), excessive angiogenesis related tumor (cancer), heart vascular diseases (for example, atherosclerosis), chronic inflammation (for example, rheumatic arthritis or Crone's disease), diabetics (for example, diabetic retinopathy), psoriasis, and endometriosis.

DETAILED DESCRIPTION OF THE INVENTION

Technical Problem

Thus, the present inventors have tried to develop a composition for anti-angiogenesis which has minimum side-effect and superior treatment effect, and have completed the present invention.

The object according to an embodiment of the present invention is to provide a peptide having an effect of anti-angiogenesis, a composition comprising thereof, and a method for treatment of angiogenesis-related diseases.

The object according to another embodiment of the present invention is to provide a composition for inhibition of tumor growth and metastasis effectively.

The object according to other embodiment of the present invention is to provide a composition for treatment and prevention of angiogenesis-related disease.

Solutions for the Problem

To achieve the said object, in an embodiment of the present invention, a composition for anti-angiogenesis comprising a peptide having an amino acid sequence of SEQ ID NO:1, a peptide having an amino acid sequence having homology 80% or more of the peptide, or a fragment of the amino acid sequence may be provided.

In the composition according to the embodiment of the present invention, the fragment may comprise 3 or more amino acids.

In the composition according to the embodiment of the present invention, the composition may inhibit proliferation of vascular endothelial cells or tube formation.

In the composition according to the embodiment of the present invention, the composition may inhibit proliferation of vascular endothelial cells by VEGF-A (Vascular endothelial growth factor-A), tube formation or invasion of endothelial cells.

In the composition according to the embodiment of the present invention, the composition may be for the prevention and treatment of angiogenesis-related diseases.

In the composition for anti-angiogenesis according to the embodiment of the present invention, the fragment may comprise 3 or more amino acids.

In the composition for anti-angiogenesis according to the embodiment of the present invention, the composition may be for the prevention or treatment of is tumor growth and metastasis, diabetic retinopathy, retinopathy of prematurity, corneal graft rejection, neovascular glaucoma, scarlet syndrome, proliferative retinopathy, psoriasis, macular degeneration, hemophilic arthropathy, capillary proliferation within atherosclerotic plaques, keloid, wound granulation, vascular adhesion, rheumatoid arthritis, chronic inflammation, osteoarthritis, autoimmune disease, Crohn's disease, restenosis, atherosclerosis, stenosis of intestine, cat scratch disease, ulcers, cirrhosis complications, glomerulonephritis, diabetic nephropathy, malignant nephrosclerosis, thrombotic micro vascular syndrome, organ transplant rejection, glomerulopathy, diabetes, or uncontrolled angiogenesis-related disorders or diseases of inflammation or neurodegeneration.

In the composition for anti-angiogenesis according to the embodiment of the present invention, the composition may be for the prevention or treatment of the tumor growth and metastasis.

In the composition for anti-angiogenesis according to the embodiment of the present invention, the composition may be for the prevention or treatment of the excessive angiogenesis-related ophthalmopathy.

In the composition for anti-angiogenesis according to the embodiment of the present invention, the ophthalmopathy may be diabetic retinopathy, retinopathy of prematurity, corneal graft rejection, neovascular glaucoma, scarlet syndrome, proliferative retinopathy, psoriasis, and macular degeneration.

In the composition for anti-angiogenesis according to the embodiment of the present invention, the composition may inhibit proliferation of vascular endothelial cells, VEGF (Vascular endothelial growth factor)-induced vascularization and invasion of vascular endothelial cells.

In the composition for anti-angiogenesis according to the embodiment of the present invention, the composition may be a pharmaceutical composition.

In the composition for anti-angiogenesis according to the embodiment of the present invention, the composition may be a food composition.

According to another embodiment of the present invention, the method for the prevention and treatment of angiogenesis-related diseases comprising a step of administering the composition to a subject may be provided.

In the composition according to an embodiment of the present invention, the angiogenesis-related diseases may be tumor growth and metastasis, diabetic retinopathy, retinopathy of prematurity, corneal graft rejection, neovascular glaucoma, scarlet syndrome, proliferative retinopathy, psoriasis, macular degeneration, hemophilic arthropathy, capillary proliferation within atherosclerotic plaques, keloid, wound granulation, vascular adhesion, rheumatoid arthritis, chronic inflammation, osteoarthritis, autoimmune disease, Crohn's disease, restenosis, atherosclerosis, stenosis of intestine, cat scratch disease, ulcers, cirrhosis complications, glomerulonephritis, diabetic nephropathy, malignant nephrosclerosis, thrombotic micro vascular syndrome, organ transplant rejection, glomerulopathy, diabetes, or uncontrolled angiogenesis-related disorders or diseases of inflammation or neurodegeneration.

In the composition according to another embodiment of the present invention, the method for treatment and prevention of angiogenesis-related diseases comprising a step of administering the composition to a subject in need of.

Effect of the Invention

According to the present invention, the composition for inhibiting effectively angiogenesis may be provided. Therefore, the composition according to the present invention may be for the treatment and prevention of angiogenesis-related diseases and especially the treatment of ophthalmopathy by the tumor growth and metastasis inhibition and excessive angiogenesis.

In addition, a peptide having an amino acid sequence of SEQ ID NO:1, a peptide having an amino acid sequence having homology 80% or more of the peptide, or a fragment of the amino acid sequence has superior anti-angiogenesis efficacy.

BRIEF DESCRIPTION OF THE DRAWINGS

In FIG. 17, HSP70 level (the left panel) and HSP90 (the right panel) were confirmed by using the serum collected from the PEP1 (50 μg/kg) or PBS (10 mice per group; n=20) treated mouse models through ELISA. In FIG. 18, the relationship between the blood level of HSP70 and the weight of tumor (the left panel) or the size of tumor (the right tumor) were analyzed ($R2=1$, versus the weight of tumor, HSP70 shows $P=0.037$, versus the size of tumor, HSP70 shows $p=0.039$, using 2-way t-test).

BEST MODE OF EXAMINING THE INVENTION

Figure 1:
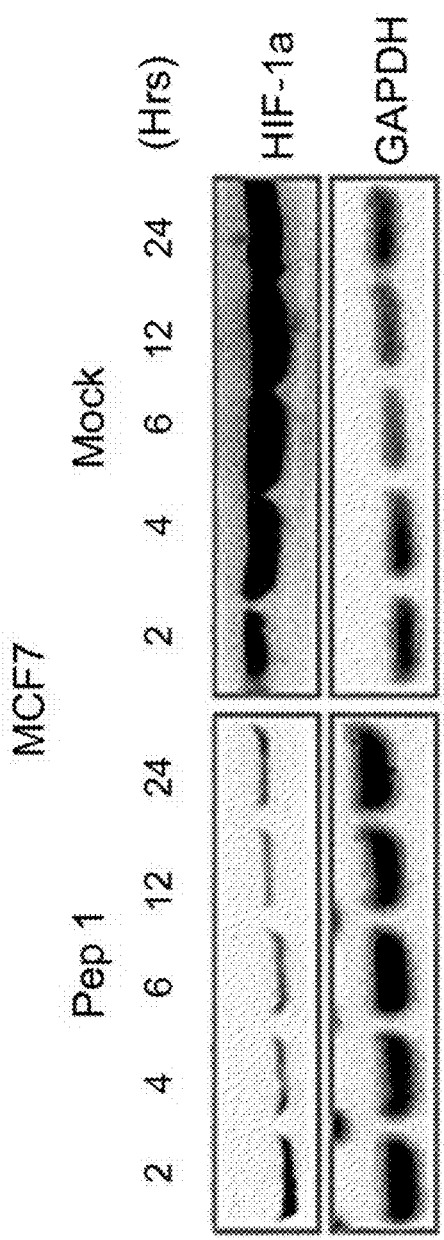
FIG. 1 and FIG. 2 are the photographs which represent the results that PEP1 inhibits HIF-1α production in hypoxia-induced cells. MCF7 and HeLa cells after treatment of PEP1 (20 μM) or vehicle, were incubated in a hypoxia circumstance during a fixed time. The cell lysate are immunoblotted for analyzing the amount of HIF-1α.

Since the present invention can be adapted to various fields of use and in various modifications, the followings are more detailed descriptions of the present invention. Nevertheless, this is no means to limit the form of practical application; it should be understood that the intention is to include the concept and the extent of technology in all of the modifications, equivalents to alternatives. In describing the present invention, if any detailed description about the prior art is considered to deteriorate the fundamental principles of the present invention, the description will be omitted.

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For example, cancer cells excrete an enzyme called telomerase, which prevents shortening of telomeres, thus resulting in proliferation of cancer cells. The inventors of the present invention have identified that a peptide derived from telomerase is effective in anti-angiogenesis and have completed the present invention.

The excessive angiogenesis is related to the disease such as cancer, age-related macular degeneration, rheumatoid arthritis, and psoriasis. If there are such diseases, by the excessive angiogenesis, making the new blood vessel to the tissue having diseases destroys the normal tissues. In case of cancer, the new blood vessels may make the tumor cells to be parasitic on other tissues by circulation.

Such angiogenesis-related disease is tumor growth and metastasis, diabetic retinopathy, retinopathy of prematurity, corneal graft rejection, neovascular glaucoma, scarlet syndrome, proliferative retinopathy, psoriasis, macular degeneration, hemophilic arthropathy, capillary proliferation within atherosclerotic plaques, keloid, wound granulation, vascular adhesion, rheumatoid arthritis, chronic inflammation, osteoarthritis, autoimmune disease, Crohn's disease, restenosis, atherosclerosis, stenosis of intestine, cat scratch disease, ulcers, cirrhosis complications, glomerulonephritis, diabetic nephropathy, malignant nephrosclerosis, thrombotic micro vascular syndrome, organ transplant rejection, glomerulopathy, diabetes, or uncontrolled angiogenesis-related disorders or diseases of inflammation or neurodegeneration for the examples, but not limited by these.

Therefore, as the treatment drugs for diabetic retinopathy, retinopathy of prematurity, retinal macular degeneration, neovascular glaucoma, retinal venous occlusive disease, retinal arterial occlusive diseases, alar plate, rubeosis, retinal angiogenesis, solid tumor, hemangioma, the growth and metastasis of tumor, searching for the useful anti-angiogenesis compound is meaningful for finding the widely usable drugs for the many diseases.

HSP90, by regulating the client proteins which are important to cell viability and tumor growth, has a tight relation to making the tumor [Calderwood S K, Trends in biochemical sciences. 31, 164-72, 2006; Garcia-Carbonero R et al, The lancet oncology, 14, e358-69, 2013]. The list of such client proteins include a tyrosine kinase receptor, a signal transfer protein, a cell cycle protein, an anti-apoptosis protein etc [Garcia-Carbonero R et al., The lancet oncology. 14, e358-69, 2013]. For these proteins, HIF-1α (alpha) plays a key role of inducing angiogenesis in hypoxia circumstance. Thus, the overexpression of HSP90 induces an increase of tumor vascularization [Sun J et al, Arteriosclerosis, thrombosis, and vascular biology, 24:2238-44, 2004; Pfosser A et al, Cardiovascular research. 65:728-36. 2005]. Both HSP70 and HSP90 are shown in the extracellular crack and the plasma membrane locally [Ferrarini M et al, International journal of cancer Journal international du cancer. 51:613-9. 1992; Vanbuskirk A et al, The Journal of experimental medicine. 170:1799-809, 1989], especially HSP70 released from tumors are tightly related to the progress and bad prognosis of some tumors [Yeh C H et al, Leukemia research, 34:605-9, 2010; Kocsis J et al, Cell stress & chaperones, 15:143-51, 2010], and the serum value of HSP70 are found to be related to the internal value of HSP70 [Dempsey N C et al, Journal of leukocyte biology, 87:467-76, 2010]. Also, the inhibition of HSP90 leads the decrease of angiogenesis and the direct cytopathic effect to cancer cells [Ganji P N et al, Angiogenesis, 16:903-17, 2013; Bohonowych J E et al, BMC cancer, 11:520, 2011]. HSP70 also has been a target for the pharmaceutical treatment, and some candidates were developed [Evans C G et al, Journal of medicinal chemistry, 53:4585-602, 2010; Powers M V et al, Cell cycle, 9:1542-50, 2010].

In the present invention, we found out the effect of PEP1 to the HIF-1α and VEGF values in cancer cell growth, normoxia circumstance and hypoxia circumstance, and did the experiment for evaluating the effect of PEP1 in vivo by using the xenograft mouse models.

In the present invention, we confirmed that when PEP1 was treated to the cancer cells, it decreases the production of HIF1-α in hypoxia circumstance, and that when PEP1 was treated to the cancer cells, it decreases the level of HSP70 and HSP90 proteins.

In an embodiment of the present disclosure, a peptide of an amino acid sequence SEQ ID NO: 1, a peptide fragment of the above-mentioned peptide or a peptide having a sequence identity of 80% or greater to the amino acid sequence of the above-mentioned peptide comprise telomerase, in particular, telomerase derived from *Homo sapiens* was included.

The peptides disclosed herein may include peptides comprising an amino acid sequence at least 80%, at least 85%, at least 90%, at least 95%, at least 96%, at least 97%, at least 98%, at least 99% of sequence homology with the peptide of SEQ ID NO: 1 or a fragment thereof. Moreover, the peptides disclosed in the present invention may include peptides having differences from SEQ ID NO: 1 or a fragment thereof in at least one amino acids, at least 2 amino acids, at least 3 amino acids, at least 4 amino acids, at least 5 amino acids, at least 6 amino acids, or at least 7 amino acids.

In one embodiment of the present invention, changes in amino acids include modifications of peptide's physical and chemical characteristics. For example, amino acid modification can be performed for improving thermal stability of the peptide, altering substrate specificity, and changing the optimal pH.

The term "amino acid" herein includes not only the 22 standard amino acids that are naturally integrated into a peptide but also the D-isomers and modified amino acids. Therefore, in a specific embodiment of the present invention, a peptide herein includes a peptide having D-amino acids. In addition, a peptide may include non-standard amino acids such as those that have been post-translationally modified. Examples of post-translational modification include phosphorylation, glycosylation, acylation (including acetylation, myristoylation, palmitoylation), alkylation, carboxylation, hydroxylation, glycation, biotinylation, ubiquitinylation, modification in chemical properties (e.g. β-removing deimidation, deamidation) and structural modification (e.g. formation of disulfide bridge). Also, changes of amino acids include the changes of amino acids that occur due to chemical reaction during the combination process with cross-linkers for formation of a peptide conjugate, such as changes in an amino group, carboxyl group or side chain.

A peptide disclosed herein may be a wild-type peptide that has been identified and isolated from natural sources. Meanwhile, when compared to SEQ ID NO: 1 or its fragments, the peptides disclosed herein may be artificial variants that comprise one or more amino acids substituted, deleted and/or inserted. Amino acid alteration in wild-type polypeptides—not only in artificial variants—comprises protein folding and/or conservative substitutions of amino acids that do not influence activities significantly. Examples of conservative substitutions may be within the groups of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activities are known in the art. Most common occurring alterations are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations thereof. Other examples of conservative substitutions are shown in the following Table 1:

| Original amino acid | Examples of residue substitution | Preferable residue substitution |
| --- | --- | --- |
| Ala (A) | val; leu; ile | Val |
| Arg (R) | lys; gln; asn | Lys |

-continued

| Original amino acid | Examples of residue substitution | Preferable residue substitution |
|---|---|---|
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |
| Ser (S) | thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

The substantial transformation of the biological properties of peptides are performed by selecting a significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in the target area, or (c) the efficacy of maintaining the bulk of the side chain. Natural residues are divided into groups by general side chain properties as the following:

(1) hydrophobicity: Norleucine, met, ala, val, leu, ile;
(2) neutral hydrophilicity: cys, ser, thr;
(3) acidity: asp, glu;
(4) basicity: asn, gin, his, lys, arg;
(5) residue that affects chain orientation: gly, pro; and
(6) aromaticity: trp, tyr, phe.

Non-conservative substitutions may be performed by exchanging a member of the above classes to that of a different class. Any cysteine residues that are not related in maintaining the proper three-dimensional structure of the peptide can typically be substituted into serine, thus increasing the oxidative stability of the molecule and preventing improper cross-linkage. Conversely, improvement of stability can be achieved by adding cysteine bond(s) to the peptide.

Another type of amino acid variants of peptides are those having a changed pattern of peptide glycosylation. The term "change" herein means deletion of at least one carbohydrate residues that are found in a peptide and/or addition of at least one glycosylated residues that do not exist within a peptide.

Glycosylation in peptides are typically N-linked or O-linked. The term "N-linked" herein refers to that carbohydrate residues are attached to the side chain of asparagine residues. As tripeptide sequences, asparagine-X-serine and asparagine-X-threonine (wherein the X is any amino acid except proline) are a recognition sequence for attaching a carbohydrate residue enzymatically to the side chain of asparagine. Therefore, with the presence of one of these tripeptide sequences in a polypeptide, the potential glycosylation sites are created. "O-linked glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of a glycosylation site to a peptide is conveniently performed by changing an amino acid sequence to contain a tripeptide sequence mentioned above (for N-linked glycosylation sites). These changes may be made by addition of at least one from serine or threonine residues to the first antibody sequence, or by substitution with these residues (for O-linked glycosylation sites).

Also the peptide according to the present invention comprising the amino acid sequence of SEQ ID NO: 1, the peptide comprising the amino acid sequence having more than 80% homology with above-mentioned sequence, or fragments of the above-mentioned peptide has the advantage of low toxicity and high stability in living matter. The SEQ ID NO: 1 as used herein is a telomerase-derived peptide comprised of 16 amino acids.

The peptide described in SEQ ID NO: 1 is same as the following table 1. The "name" in Table 2 below was for distinction of peptides. In one aspect, the peptide of SEQ ID NO: 1 is the entire peptide of a human telomerase. In a different specific embodiment of the present invention, the peptide having a sequence of SEQ ID NO: 1, the peptide which is a fragment of the peptide having the sequence of SEQ ID NO: 1 or the peptide having 80% or more sequence identity with the peptide according to the present disclosure includes "synthetic peptides" synthesized by selecting and synthesizing a peptide corresponding to the pertinent position within the telomerase. SEQ ID NO: 2 is the amino acid sequence of the entire telomerase.

TABLE 2

| SEQ ID No. | Name | PROSITION IN TELOMERASE | SEQUENCE | LENGTH |
|---|---|---|---|---|
| 1. | pep1 | [611-626] | EARPALLTSRLRFIPK | 16 aa |
| 2. | Telomerase | [1-1132] | MPRAPRCRAVRSLLRSHYREVLPLATFVRRLGPQGWR LVQRGDPAAFRALVAQCLVCVPWDARPPPAAPSFRQV SCLKELVARVLQRLCERGAKNVLAFGFALLDGARGGP PEAFTTSVRSYLPNTVTDALRGSGAWGLLLRRVGDDV LVHLLARCALFVLVAPSCAYQVCGPPLYQLGAATQAR PPPHASGPRRRLGCERAWNHSVREAGVPLGLPAPGAR RRGGSASRSLPLPKRPRRGAAPEPERTPVGQGSWAHP GRTRGPSDRGFCVVSPARPAEEATSLEGALSGTRHSHP SVGRQHHAGPPSTSRPPRPWDTPCPPVYAETKHFLYSS GDKEQLRPSFLLSSLRPSLTGARRLVETIFLGSRPWMP GTPRRLPRLPQRYWQMRPLFLELLGNHAQCPYGVLLK THCPLRAAVTPAAGVCAREKPQGSVAAPEEEDTPPRR LVQLLRQHSSPWQVYGFVRACLRRLVPPGLWGSRHN | 1132 aa |

TABLE 2-continued

| SEQ ID No. | Name | PROSITION IN TELOMERASE | SEQUENCE | LENGTH |
|---|---|---|---|---|
| | | | ERRFLRNTKKFISLGKHAKLSLQELTWKMSVRDCAWL | |
| | | | RRSPGVGCVPAAEHRLREEILAKFLHWLMSVYVVELL | |
| | | | RSFFYVTETTFQKNRLFFYRKSVWSKLQSIGIRQHLKR | |
| | | | VQLRELSEAEVRQHREARPALLTSRLRFIPKPDGLRPIV | |
| | | | NMDYVVGARTFRREKRAERLTSRVKALFSVLNYERA | |
| | | | RRPGLLGASVLGLDDIHRAWRTFVLRVRAQDPPPELY | |
| | | | FVKVDVTGAYDTIPQDRLTEVIASIIKPQNTYCVRRYA | |
| | | | VVQKAAHGHVRKAFKSHVSTLTDLQPYMRQFVAHLQ | |
| | | | ETSPLRDAVVIEQSSSLNEASSGLFDVFLRFMCHHAVRI | |
| | | | RGKSYVQCQGIPQGSILSTLLCSLCYGDMENKLFAGIR | |
| | | | RDGLLLRLVDDFLLVTPHLTHAKTFLRTLVRGVPEYG | |
| | | | CVVNLRKTVVNFPVEDEALGGTAFVQMPAHGLFPWC | |
| | | | GLLLDTRTLEVQSDYSSYARTSIRASLTFNRGFKAGRN | |
| | | | MRRKLFGVLRLKCHSLFLDLQVNSLQTVCTNIYKILLL | |
| | | | QAYRFHACVLQLPFHQQVWKNPTFFLRVISDTASLCY | |
| | | | SILKAKNAGMSLGAKGAAGPLPSEAVQWLCHQAFLL | |
| | | | KLTRHRVTYVPLLGSLRTAQTQLSRKLPGTTLTALEAA | |
| | | | ANPALPSDFKTILD | |

In one embodiment of the present invention provides the pharmaceutical composition comprising the peptide comprising the amino acid sequence of SEQ ID NO: 1, the peptide comprising the amino acid sequence having more than 80% homology with above-mentioned sequence, or fragments of the above-mentioned peptide having anti-angiogenesis activity as an active ingredient.

The composition for anti-angiogenesis according to the one embodiment of the present invention may contain 0.01 g/L to 1 kg/L, specifically 0.1 g/L to 100 g/L, more specifically 1 g/L to 10 g/L of a peptide comprising amino acid sequence of at least one of SEQ ID NO: 1, a peptide comprising an amino acid sequence at least 80% sequence homology with the above-mentioned sequences, or a fragment of the above-mentioned thereof. When the peptide is contained in the above-mentioned ranges, both of safety and stability of the composition can be satisfied and the ranges are appropriate in terms of cost-effectiveness.

The composition according to one embodiment of the present invention, may have applications with all animals including human, dog, chicken, pig, cow, sheep, guinea pig, and monkey.

The composition according to one embodiment of the present invention, may provide the pharmaceutical composition for inhibiting angiogenesis which comprises the peptide comprising the amino acid sequence of SEQ ID NO: 1, the peptide comprising the amino acid sequence having more than 80% homology with above-mentioned sequence, or fragments of the above-mentioned peptide. In the pharmaceutical composition according to one embodiment of the present invention may be administered through oral, rectal, transdermal, intravenous, intramuscular, intraperitoneal, in the bone marrow, epidural or subcutaneous routes.

Forms of oral administration may be, but not limited to, tablets, pills, soft or hard capsules, granules, powders, solution, or emulsion. Forms of non-oral administration can be, but not limited to, injections, drips, lotions, ointments, gels, creams, suspensions, emulsions, suppository, patch, or spray.

The pharmaceutical composition according to one embodiment of the present invention, if necessary, may contain additives, such as diluents, excipients, lubricants, binders, disintegrants, buffers, dispersants, surfactants, coloring agents, aromatics or sweeteners. In one embodiment of the present invention, the pharmaceutical composition may be manufactured by conventional methods of the industry in the art.

The dose of the active ingredient of the pharmaceutical composition according to one embodiment of the present invention, may vary according to the patient's age, sex, weight, pathology and state, administration route, or prescriber's judgment. Dosage based on these factors may be determined within levels of those skilled in the art, and the daily dose, for example, may be, but not limited to, 10 ng/kg/day to 10 mg/kg/day, specifically 0.1 µg/kg/day to 1 mg/kg/day, more specifically the 1 µg/kg/day to 100 µg/kg/day, more specifically the 2 µg/kg/day to 50 µg/kg/day, but it can be adjusted if there is the differences of the effect according to administration dosage. In one embodiment of the present invention, the pharmaceutical composition may be administered, but not limited to, 1 to 3 times a day.

In one embodiment of the present invention provides the food composition for anti-angiogenesis which comprises the peptide comprising the amino acid sequence of SEQ ID NO: 1, the peptide comprising the amino acid sequence having more than 80% homology with above-mentioned sequence, or fragments of the above-mentioned peptide.

In one embodiment of the present invention, food composition is not limited to specific forms, but, for example, may be tablets, granules, powder, liquid, and solid forms. Each form may be formed with ingredients commonly used in the industry appropriately chosen by those skilled in the art, in addition to the active ingredient, and may produce a synergic effect in combination of other ingredients.

The terms used herein is intended to be used to describe the embodiments, not to limit the present invention. Terms without numbers in front are not to limit the quantity but to show that there may be more than one thing of the term used. The terms "comprising", "having", "including" and "containing" shall be interpreted openly (i.e. "including but not limited to").

The reason why the numeric values are mentioned as the ranges is only because it is convenient to describe in the range rather than individual numbers. Unless otherwise noted, each individual numeric values should be understood to be described individually and integrated into the specification. Thresholds in all ranges are included and can be combined independently.

Unless otherwise noted or clearly contradicting in context, all methods mentioned herein can be performed in a proper order. The use of any one embodiment and all embodiment, or exemplary language (e.g., "such as", "like~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meanings ordinarily understood by a person skilled in the art that the present invention belongs to.

The preferred embodiments of the present invention include the best mode known to the inventors to perform the present invention. Variations in the preferred embodiments can become clear to those skilled in the art after reading the statements above. The present inventors' hope that those skilled in the art can use the variations adequately and present invention be conducted in other ways than listed herein. Thus, the present invention, as allowed by the patent law, includes equivalents, modifications and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

In the embodiments as below, by using Human umbilical vein endothelial cell (HUVEC), it was tried to confirm the direct inhibition effect of PEP1 to the proliferation of vascular endothelial cells, the vascularization and the cell invasion.

EMBODIMENTS FOR ESTABLISHING THE PRESENT INVENTION

Hereinafter, the present disclosure will be described in detail through examples and test examples. However, the following examples and test examples are for illustrative purposes only and it will be apparent to those of ordinary skill in the art that the scope of the present disclosure is not limited by the examples and test examples.

Example 1: Synthesis of a Peptide

The peptide of SEQ ID NO: 1 was synthesized according to the conventionally known method of solid phase peptide synthesis. More specifically, the peptide was synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to a resin were used as follows:

NH2-Lys(Boc)-2-chloro-Trityl Resin
NH2-Ala-2-chloro-Trityl Resin
NH2-Arg(Pbf)-2-chloro-Trityl Resin All the amino acids to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in an acid. Examples include the followings:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetamethylaminium hexafluorophosphate]/HOBt [N-Hydroxybenzotriazole]/NMM [4-Methylmorpholine] were used as the coupling reagents. Piperidine in 20% DMF was used to remove Fmoc. In order to remove the protection from residues or to separate the synthesized peptides from Resin, cleavage cocktail [TFA (trifluoroacetic acid)/TIS (triisopropylsilane)/EDT (ethanedithiol)/H2O=92.5/2.5/2.5/2.5] was used.

The peptide synthesis was performed by using solid phase scaffold with the repetition of the following processes: starting with the amino acid protection, separate reaction of each amino acid, washing with solvents, and deprotection. Each peptide was synthesized by using the solid phase scaffold combined to starting amino acid with the amino acid protection, reacting the corresponding amino acids separately, washing with a solvent and deprotected, and repeating the processes. Upon the release from the resin, the synthesized peptides were purified by HPLC, validated by Mass Spectrometry, and freeze-dried, and verify for synthesis by MS, and then freeze-dried.

The purity of the prepared peptide was found to be 95% or higher by high-performance liquid chromatography.

Specific synthesis process of PEP1 may be as follows:
1) Coupling

The amino acid (8 equivalents) protected with NH2-Lys(Boc)-2-chloro-Trityl Resin, and coupling agent HBTU (8 equivalents)/HOBt (8 equivalents)/NMM (16 equivalents) melted in DMF were mixed together, and incubated at room temperature (RT) for 2 hr. Following the incubation, the reaction mixture was subjected to the sequential washes of DMF, MeOH, and DMF.

2) Fmoc deprotection

Piperidine in 20% DMF was added and incubated at RT for 5 minutes 2 times, then sequentially washed with DMF, MeOH, and DMF.

3) Making the basic framework of peptide, NH2-E(OtBu)-A-R(Pbf)-P-A-L-L-T(tBu)-S(tBu)-R(Pbf)L-R(Pbf)-F-I-P-K(Boc)-2-chloro-Trityl Resin) by repeating the above mentioned-reactions 1) and 2).

4) Cleavage: Cleavage Cocktail was added to the completely synthesized peptide, thus separating the synthesized peptide from the resin.

5) Pre-chilled diethyl ether was added into the obtained mixture, and then centrifugation was used to precipitate gathered peptide.

6) After purification by Prep-HPLC, the molecular weight was confirmed by LC/MS and lyophilized to produce in a powder form.

Example 2: Incubation of Cell Lines and Analysis Method

Incubation of Cell Lines

MCF7 (the human breast adenocarcinoma) cell line, Jurkat (the human T-lymphocyte) cell line, and MC38 (the murine colon adenocarcinoma) cell line were maintained in the 10% fetal bovine serum and the 100 U/ml penicillin and streptomycin added RPMI 1460 media. HeLa (human cervical adenocarcinoma) cell line was maintained in the 10% fetal bovine serum and the 100 U/ml penicillin and streptomycin added DMEM (Dulbecco's modified Eagle's medium) media.

Verification of the Protein Expression and Cell Growth in Hypoxia Circumstance

In hypoxia circumstance, for verifying the effect of PEP1 to the level of HSP, MCF7 and HeLa cells were treated with 20 μM PEP1, and incubated in the hypoxia circumstance and the normoxia circumstance. By using BBL GasPak (Becton Dickinson) which lows the oxygen to non-detective level in 90 minutes by catalytic reaction, the anoxia circumstance was induced. The incubation time was in a range of 2 to 24 hours. As mentioned above, the cells were collected and immunoblotted by using α-HSP70, α-HSP90, α-HIF-1α, or α-GAPDH antibodies. The α-GAPDH, for the protein quantification, was used for the normalization of the amount of HSP70/90 by the amount of GAPDH.

For verifying the effect of PEP1 to the cancer cell growth in the hypoxia circumstance, MCF7 and HeLa cells were seeded to 96-well plate of the 1×104 cells per well and incubated in the 10% FBS added complete media of the 37° C., 5% CO2 circumstance. After treating the serum starvation in 2 hours, it was incubated in the complete media with or without PEP1 (20 μM). As mentioned above, the cells were incubated for 1 day to 6 days in the hypoxia circumstance or the normoxia circumstance. The number of viable cells were measured by the tryphan blue exclusion staining method. All of the calculation experiments were repeated.

Analyzation Method for HSP70 and HSP90 Protein Level by the Immunoblotting

Jurkat and MCF7 cells (5×105) were seeded and incubated for 12 hours.

After treating the starvation for 2 hours by adding the OPTI-MEM media, same as the shown figure, the cells were treated by the PEP1 at the different concentrations, by the scrambled peptides, 1-AAG (1 μM) or KNK437 (1 μM). After the 2-hour incubation, the cells were collected and lysated by using cell lysis buffer (Thermo Scientific, IL, USA). By using Bradford Protein Assay (Bio-Rad, USA), the protein concentration was quantified, and the samples were treated by SDS-PAGE and immunoblotting with α-HSP70 (sc-32239 and sc-66048, Santa Cruz, Calif., USA), α-HSP90 (ab1429, abcam, USA), α-GRP78 (sc-13968), α-HIF-1a (sc-10790) or α-GAPDH (sc-25778) antibodies. The immune reactive band was visualized by the intensive chemiluminescence kit (iNtRoN Biotechnology, INC, Korea), and analyzed by ImageQuant™ LAS-4000 (GE Healthcare Life Science, NJ, US).

Analyzation Method for HSP70 and HSP90 Protein Levels by the Flow Cytometry

MCF7 cells were treated by the PEP1 or the control group. For the proteasome inhibition test, during the incubation, the cells were treated by the 5 μM proteasome inhibitor MG132 (Calboicam). By using the trypsin, the cells were separated and rinsed by the cold PBS (phosphate buffered saline) and the FACS buffer (PBS containing 1% BSA and 0.1% NaN3). For the intracellular staining, the cells were treated by the permeabilization buffer (eBioscience, CA, USA) following the instruction of the manufacturer. The cells were reacted with α-HSP70-FITC (ab61907, Abcam) or α-HSP90-PE (ab65171, Abcam) at the 4° C. for 30 minutes. By using FACScan flow cytometer (Becton Dickinson Co., CA, USA), the flow cytometry analysis was done. The data were analyzed by using Flowjo™ software (version 10.0.5, Tree Star, Inc., OR, USA).

Method for Evaluating the Effect of the PEP1 to Tumor Growth In Vivo 7 week-old BALB/c athymic mice (Nu/Nu) (10 mice per group; n=20, female, Orient Bio Co. Gyunggido, Korea) were divided into two groups randomly after the subcutaneous injection of murine colon carcinoma MC38 (5×105 cells/ml in 200 μl PBS per site). PEP1 (50 μg/kg in 100 μl 0.9% NaCl solution) or PBS were injected into the mice once per 2 days. When the size of tumor reaches 10 mm, the PEP1 and PBS were injected to the inside of tumor. The size of tumor was measured in once per 2 days, and the volume of tumor was calculated following equation; volume (mm3)=((width2×length)/2). All experiments were approved by the Institute for Experimental Animals (College of Medicine, Seoul National University at Seoul, Korea).

Evaluation for the Proliferated Cells and the Apoptosis in the Tumor Section

For evaluating the apoptosis of tumor, by using formalin-fixed and Paraffin-embedded tumor sections, the DNA fragmentation was analyzed by Tunnel assay. According to the manufacturer's instruction, the tumor section was stained by the apoptosis detection kit (ApopTag Peroxidase In Situ, Millipore). The proliferating cells in tumor were detected by using PCNA (Proliferating cell nuclear antigen). For searching the antigen, the tissue sections were deparaffinized in 10 μM citrate (pH6.0) buffer during 40 minutes, hydrated, and heated. The tissues were stained by anti-mouse PCNA monoclonal antibody (ab29, Abcam). After the second treatment and development of antibody, the tissue sections were contrast stained by H&E staining method. And then, the field was randomly selected from the 6 slides of each treatment groups, and the field was analyzed by Leica Qwin software for quantification.

Immunoblotting Analysis for HSP Expression in Tumor

Similar to the PCNA staining method, by using immunohistochemical staining, HSP70 and HSP90 proteins expression in tumor were evaluated. The antibodies to the heat shock proteins (HSP70; sc-7298, HSP90; ab1429) was used as the first antibodies. HSP70 and HSP90 proteins expression by tumors was evaluated by immunoblotting using tumor lysate. After freezing by liquid oxygen, the tumor was crashed by the mortar, and homogenized by extraction buffer (20 mM HEPES, pH7.5, 100 mM NaCl, 0.05% Triton X-100, 1 mM DTT, 0.5 mM sodium orthovanadate, 1 mM EDTA, 0.5 mM PMSF, 10 μg/ml aprotinin, 5 μg/ml leupeptin, 2 μg/ml pepstatin). After repeating centrifugation, as stated above, the supernant was used for SDS-PAGE and immunoblotting.

ELISA (Enzyme-Linked ImmunoSorbent Assay) Analysis

VEGF secretion in cancer cells was confirmed by ELISA (Enzyme-linked immunosorbent assay). MCF7 and HeLa cells were incubated in the hypoxia circumstance or the normoxia circumstance after adding PEP1 or vehicle during 24 hours. The amount of VEGF in the cell supernant was confirmed by human VEGF immune analysis kit (R&D Systems, USA) following the instruction of the manufacturer. For analyzing the concentration of HSP70 and HSP90 in blood, the blood was collected from the mouse model having tumor. After the preparation of the serum, the concentration of HSP70 and HSP90 in blood was confirmed by the immune analysis kit for HSP70 (R&D systems, USA) and HSP90 (Cusabio Biotech co., Ltd, DE, USA).

Confocal Microscope Analysis

The sliced tumor section was fixed in 4% paraformaldehyde in room temperature during 15 minutes. It was rinsed by PBS 2 times, incubated in PBS with 0.25% Triton X-100 during 10 minutes, and rinsed by PBS 3 times again. After blocking the tissue in 1% BSA-PBST during 30 minutes, it was incubated with the mixture of the mouse anti-Tie2 (557039, BD Pharmigen) and the anti-CD11b (rat anti-CD11b antibodies, ab8878, abcam) antibodies in the 4° C. humidified chamber. After rising, the tissues were incubated with the mixture of AlexaFlour 488 goat anti-mouse IgG and AelxaFlour633 goat anti-rat IgG. For visualizing the cell nucleus, it was incubated with DAPI (Sigma Aldrich) during 1 minute and analyzed by the confocal microscope.

Statistical Analysis Method

The statistical comparison between the control and treated groups was done by the student's t-test. When the p-value is same or under 0.05 (p≤0.05), it is considered to be significant.

Example 3: Verification of Inhibiting the HIF-1α and VEGF Production Induced by Hypoxia HIF-1α (Hypoxia Inducible Factor-1 alpha) is known as the material which was activated by reaction with the hypoxia stimulation, the various growth factors and cytokines. Also, VEGF (Vascular Endothelial Growth Factor) is regulated by HIF-1α and stimulates the angiogenesis directly.

In this example and the present invention, the effect of PEP1 to HIF-1α protein level in the hypoxia circumstance was verified and, because HIF-1α is known for regulating VEGF (Vascular Endothelial Growth Factor) production, it was verified whether the treatment of PEP1 affect the synthesis of VEGF induced by the hypoxia circumstance or not.

Figure 2:
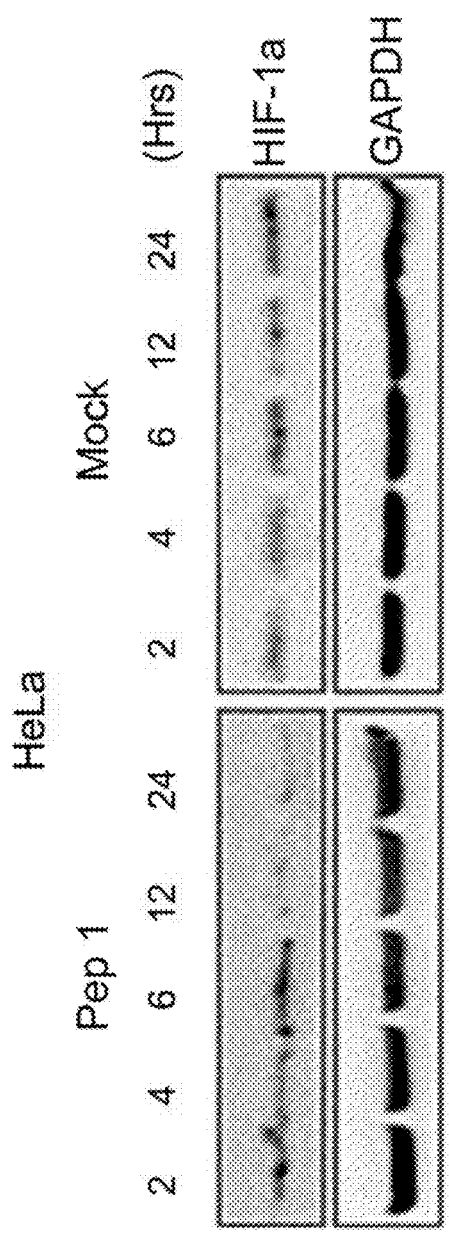

As the expression level of HIF-1α, the amount of HIF-1α in MCF7 and HeLa cells was decreased over time in the hypoxia circumstance (See FIGS. 1 and 2). Thus, the expression of HIF-1α was increased by the hypoxia circumstance in the mock treated control group, but it was very decreased in the cell of the PEP1 treated group.

Figure 3:
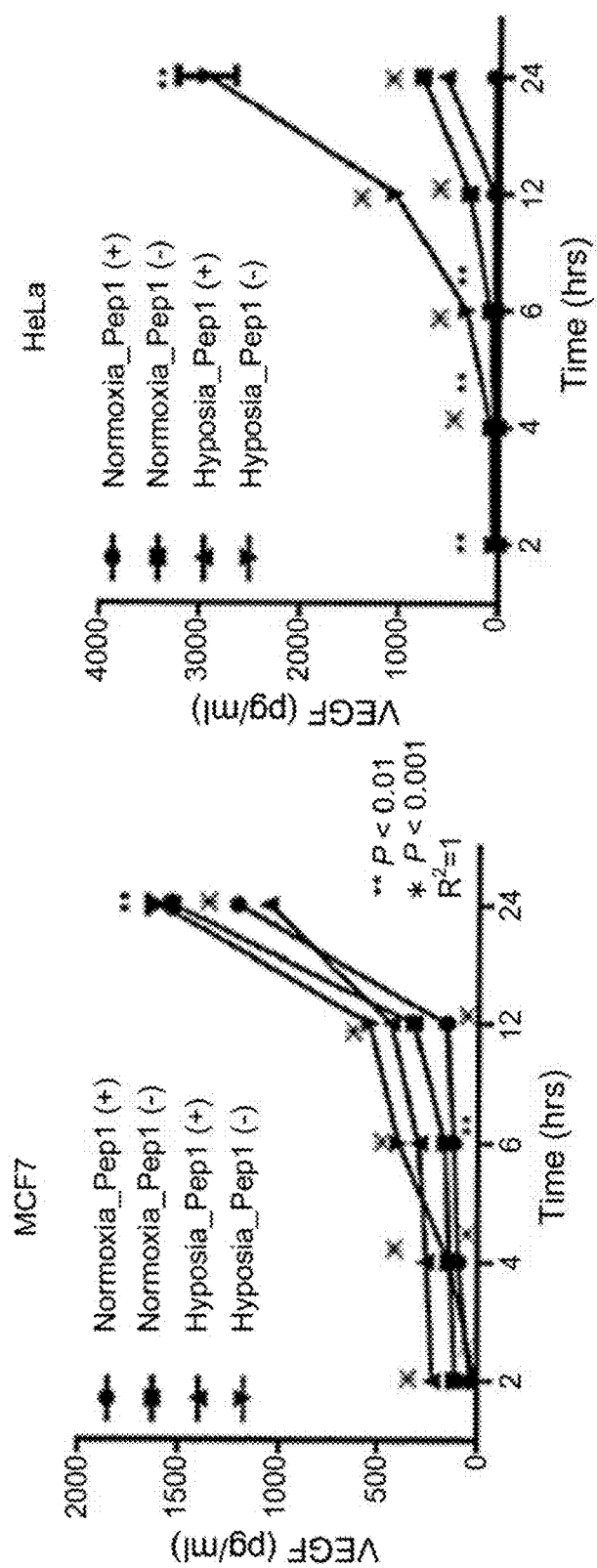
FIG. 3 is a graph which represents the inhibition of VEGF production in hypoxia circumstance induced by PEP1. MCF7 an HeLa cells were treated by PEP1 (20 μM) or vehicle and be incubated in normoxia circumstance and in hypoxia circumstance during the appointed time. The amount of VEGF secreted in the cell incubation supernant was confirmed by ELISA (versus mock, *means $p<0.05$, **means $p<0.01$, ※ means $p<0.001$ respectively).

As the result of the experiment, the amount of the secreted VEGF was increased by the induced hypoxia circumstance. However, it was confirmed that the amount of the secreted VEGF was decreased by the treatment of PEP1 (See FIG. 3).

Example 4: Verification of Inhibiting the Expression of HSP70 and HSP 90 by the Treatment of PEP1

Figure 4:
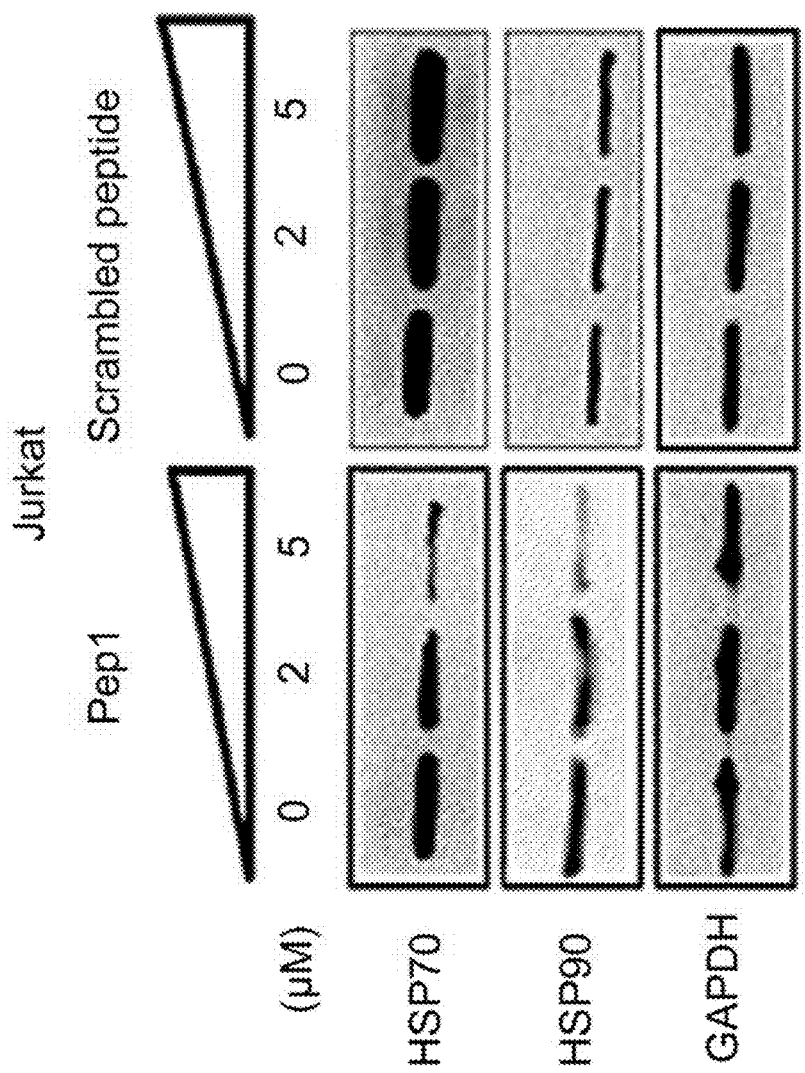
FIGS. 4 and 5 are the results of the down-regulation of HSP70 and HSP90 by treating PEP1 in tumor cells. Jurkat (FIG. 4) and MCF7 (FIG. 5) cells, in serum-free media, were treated by increasing the concentration of PEP1 or scrambled peptide for 2 hours. The amount of HSP70 and HSP90 peptides are analyzed by immunoblotting using antibodies of HSP70, HSP90 and GAPDH.
Figure 5:
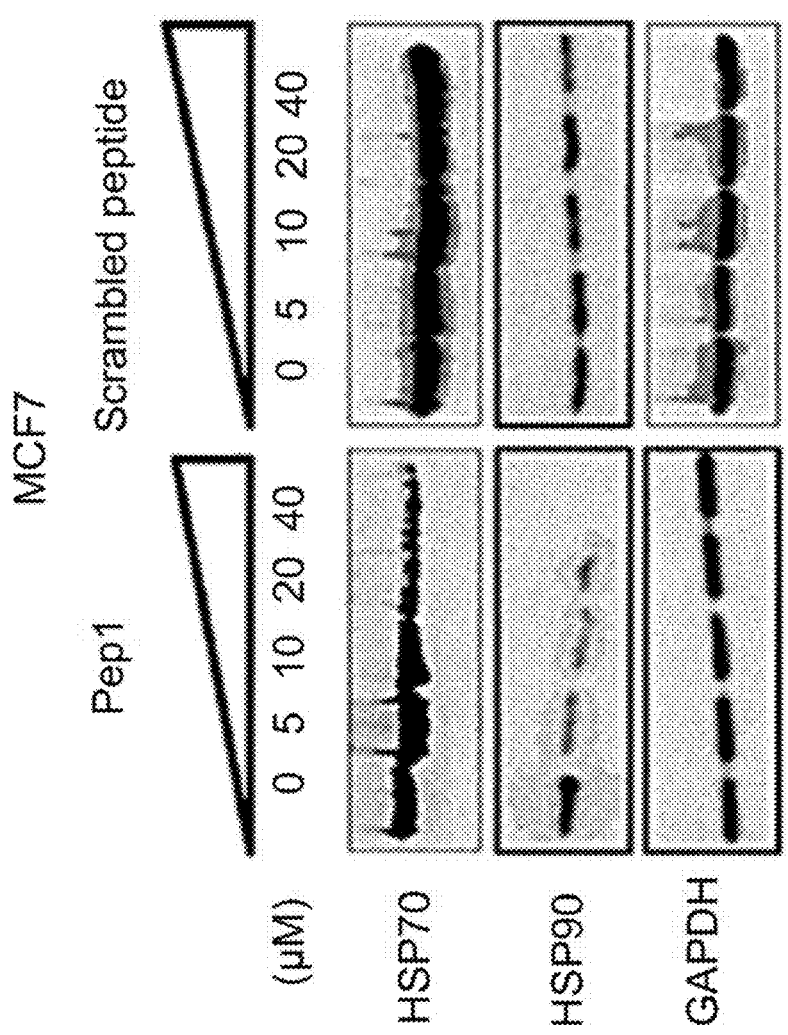

As HIF-1α which affect angiogenesis was known as a HSP client protein, in this example, it was confirmed whether the PEP1 affects the protein levels of HSP70 and HSP90. As mentioned in FIG. 4 and FIG. 5, if the PEP1 was treated for 2 hours, it significantly decreased HSP70 and HSP90 in Jurkat T-cell lymphocyte and MCF7 breast cancer cell both. In the experiment using Jurkat cells, 5 µM PEP1 decreased HSP70 and HSP90 more than 50%.

In MCF7 cells, 5 µM PEP1 treatment group decreased HSP90 more than 20% as compared with the control group. In the 20 µM PEP1 treatment group decreased HSP70 to 50% as compared with the control group. However, in the scrambled peptides which has a similar sequence not the same as the PEP1, the peptide did not affect to the level of HSP70 and HSP90 (See FIGS. 4 and 5).

Figure 6:
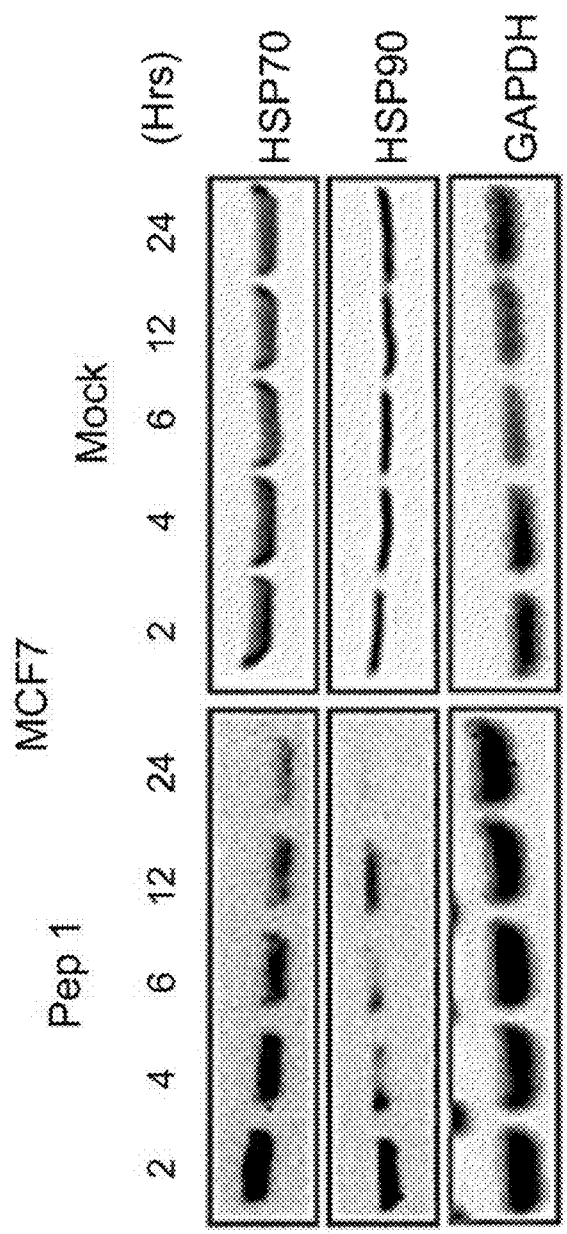
FIGS. 6 and 7 are the experimental results demonstrating the inhibition of HSP production in hypoxia-induced circumstance by PEP1. MCF and HeLa cells were treated by PEP1 (20 μM) or vehicle and be incubated in hypoxia circumstance during the fixed time. The cell lysates are immunoblotted for analyzing the amount of HSP70 and HSP90.
Figure 7:
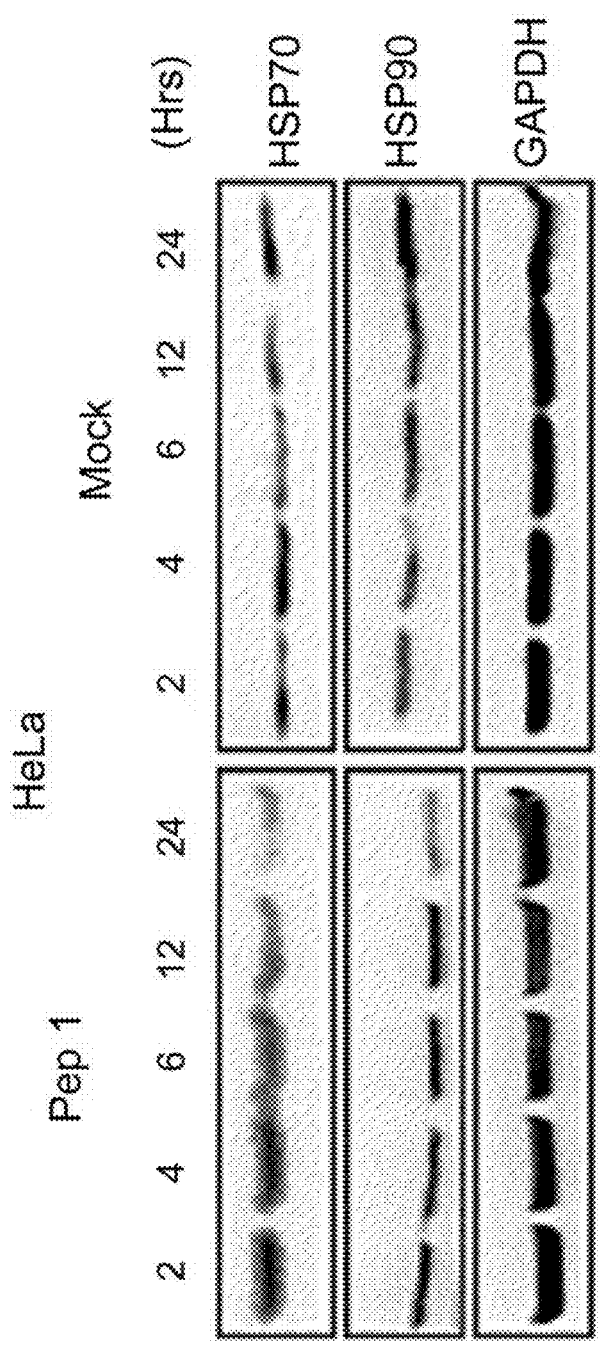

Also, same as the experiment mentioned in example 3 which verified the PEP1 effect to HIF-1α in the hypoxia circumstance was done to HSP70 and HSP90. These results are shown in the FIG. 6 and FIG. 7. As mentioned in the FIG. 6 and FIG. 7, it was verified in MCF7 and HeLa cells that the expressions of HSP70 and HSP90 were not affected over time in the mock treated control group but it was significantly decreased in the cells of the PEP1 treatment group. It clearly confirms that the treatment of PEP1 leads to the degradation of HSP and regulates its client proteins (See FIGS. 1, 2, 6 and 7). These results show that PEP1 can affect the various hypoxia circumstance-related cell reaction by decreasing the level of HSP protein.

Figure 8:
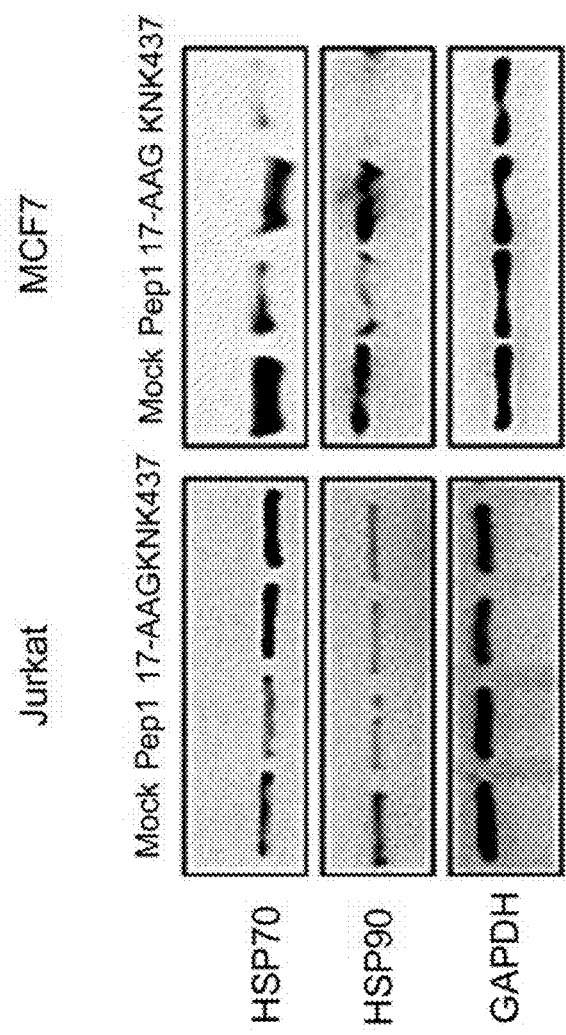
FIG. 8 is the result showing that Jurkat and MCF7 cells were treated by vehicle, PEP1, 17-AAG, and KAK437. Jurkat and MCF7 cells, in serum-free media, were treated by vehicle, PEP1 (5 μM for Jurkat and 20 μM for MCF7), 17-AAG (1 μM), KNK437 (1 μM) for 2 hours. The cell lysate was analyzed by immunoblotting in the similar way used in FIG. 4.

Next, the activity of the inhibition of HSP by PEP1 was compared with the activity of the inhibition of HSP by 17-AAG and KNK437 as known as the inhibitor of HSP90 and HSP70 respectively. 17-AAG inhibits HSP90 by inhibiting the activity of HSP90 ATPase [Uehara Y, Current cancer drug targets, 3:325-30, 2003]. KNK437 inhibits the synthesis of HSP induced by stress. In the results, only PEP1 decreased the levels of HSP70 and HP90 in Jurkat and MCF cells (See FIG. 8).

In Jurkat cells only PEP1 decreased the levels of HSP70 and HSP90 protein, and 17-AAG and KNK437 decreased the amount of HSP90 but not the amount of HSP70. In case of MCF7 cells, PEP1 and KNK437 decrease the amounts of HSP90 and HSP70 both, but 17-AAG shows very little effect on the levels of HSP90 and HSP70.

Figure 9:
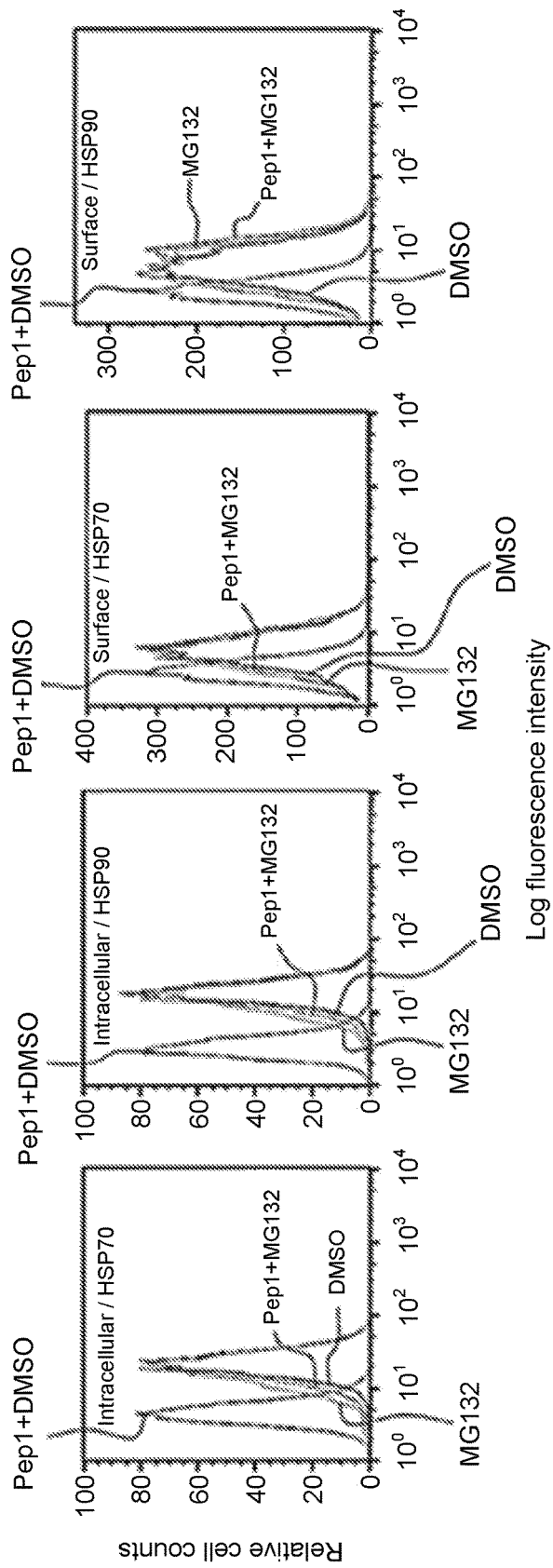
FIG. 9 is the result that MCF7 cells, with or without MG132 (5 μM), were treated by PEP1 or PBS. The intracellular HSP and extracellular HSP were dyed by using surface intracellular staining and surface staining, as mentioned materials and method, and were analyzed by flow cytometry (red color: DMSP; blue color: PEP1+DMSO; orange color: PEP1+MG132; green color: MG132).

Decreases of HSP90 and HSP70 by PEP1 were more clearly verified by Flow Cytometric Analysis. By the cell surface staining of HSP90 and HSP70 and the intracellular staining, it was shown that the treatment of PEP1 less affected the cell surface HSP than the intracellular HSP but it decreases HSP90 and HSP70 in the intracellular and the cytoplasm (See FIG. 9). In case of treating PEP1 with the proteasome inhibitor MG132, the effect by the PEP1 disappeared, and it suggests that the PEP1 can lead to proteasome-dependent degradation of HSP90 and HSP70 (See FIG. 9).

Figure 10:
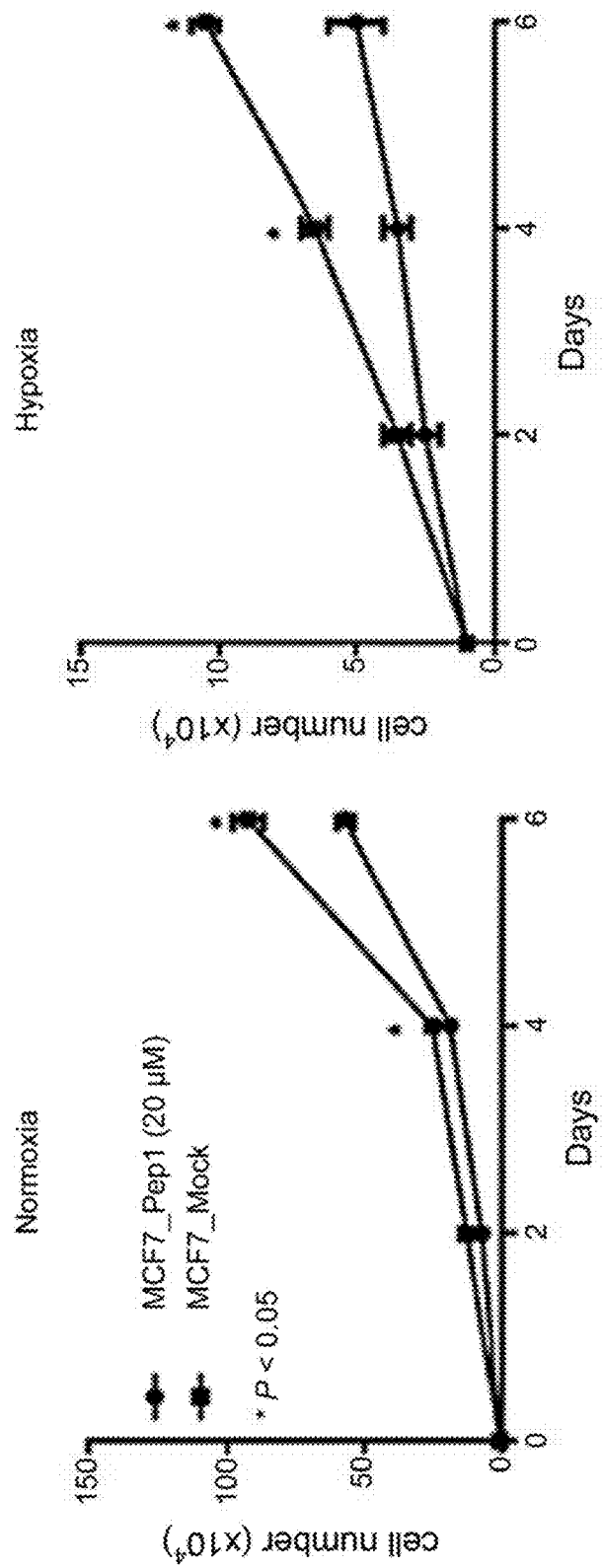
FIGS. 10 and 11 are the graphs which represent the inhibition of the proliferation of cancer cells by PEP1 in hypoxia circumstance. MCF7 and HeLa cells in normoxia circumstance (the left panel) or in hypoxia circumstance (the right panel) were incubated with or without PEP1. On day 2, day 4, day 6 of the incubation, the number of cells were counted (representation of data by mean±SD, versus mock, *means $p<0.05$, 1-way t-test were used).
Figure 11:
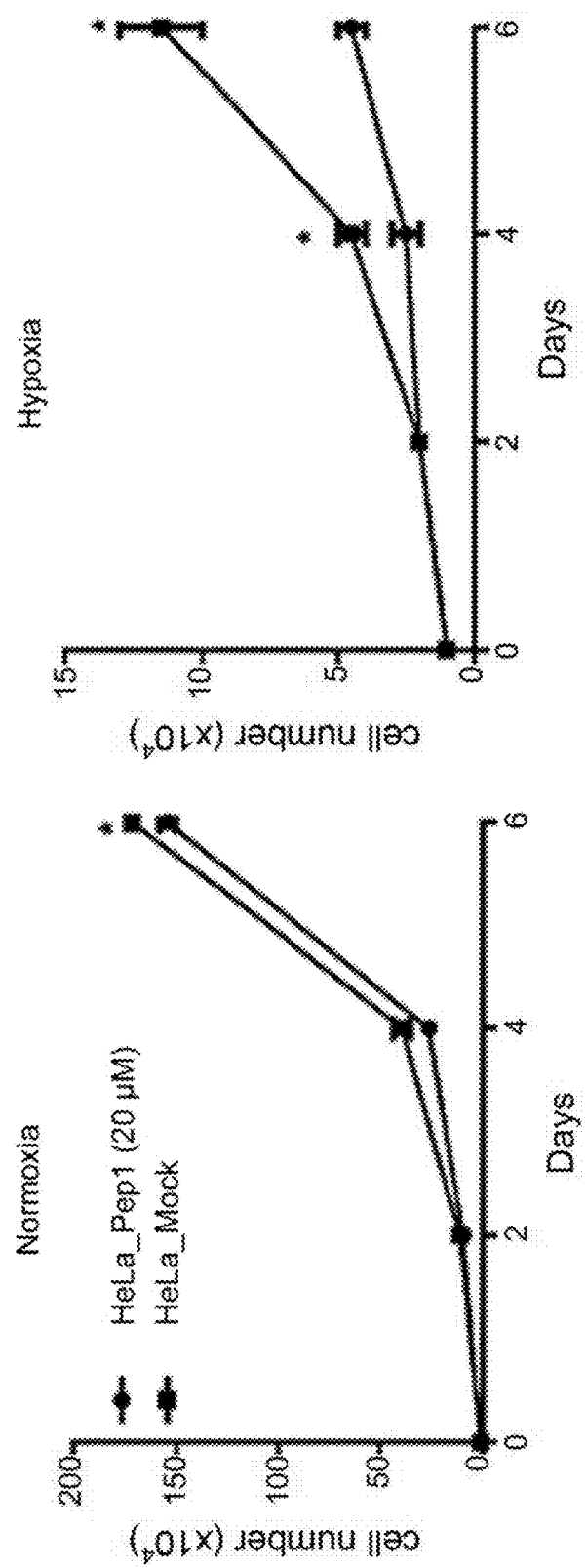

Example 5: Verifying the Tumor Growth in the Hypoxia Circumstance and the Normoxia Circumstance Similar to the examples 3 and 4, it was studied that the effect of PEP1 to tumor cell growth in the hypoxia circumstance and the normoxia circumstance. PEP1 inhibited little the MCF7 and HeLa cell growths in the normoxia circumstance, but its inhibition effect was significantly increased in the hypoxia circumstance (See FIGS. 10 and 11).

Example 6: Effect of PEP1 to Tie2+ Monocytes Recruitment in Tumor

Figure 12:
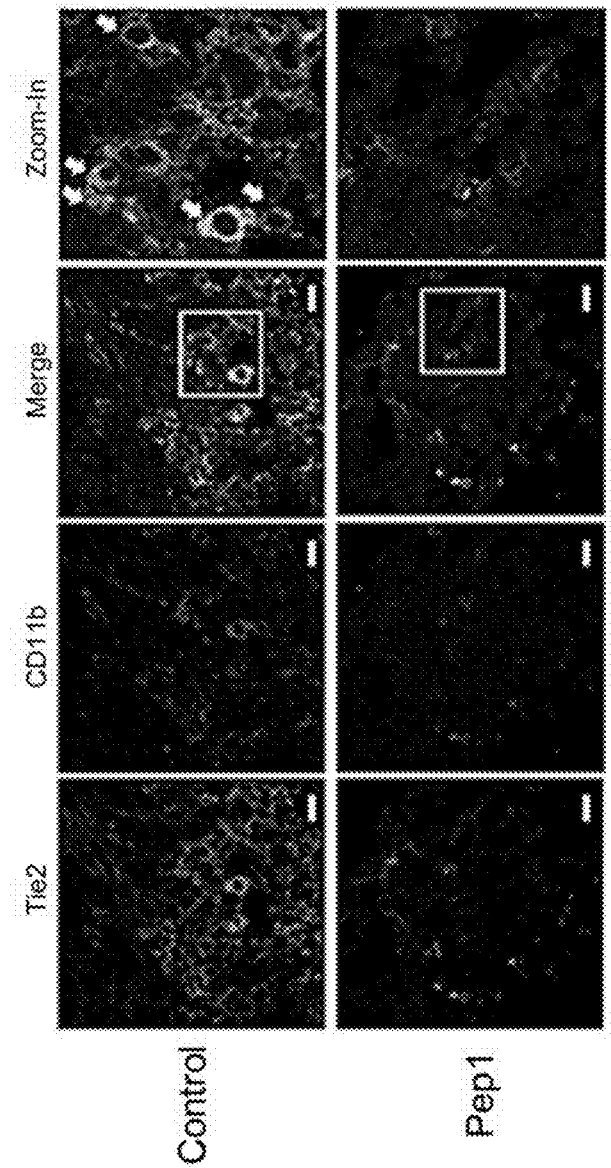
FIGS. 12 and 13 are the results which represent the effect of PEP1 to Tie2+ monocyte population in tumor cells. Tie2+ CD11b+ monocyte population were analyzed by immunofluorescence staining to detection of Tie2 (Green, AlexaFlour 488) and CD11b (Red, AlexaFlour 633). By using DAPI staining, the cell nuclear were visualized. The scale bar represents 50 μM. The arrows in the megascopic images represent Tie2+ CD11b+. Macrophage were represented per hpf. The 5 fields were selected randomly from each 2 slides of tumor tissue treatment group for quantification (*means $p<0.05$, means $p<0.01$, *means $p<0.001$, using 2-way-test).
Figure 13:
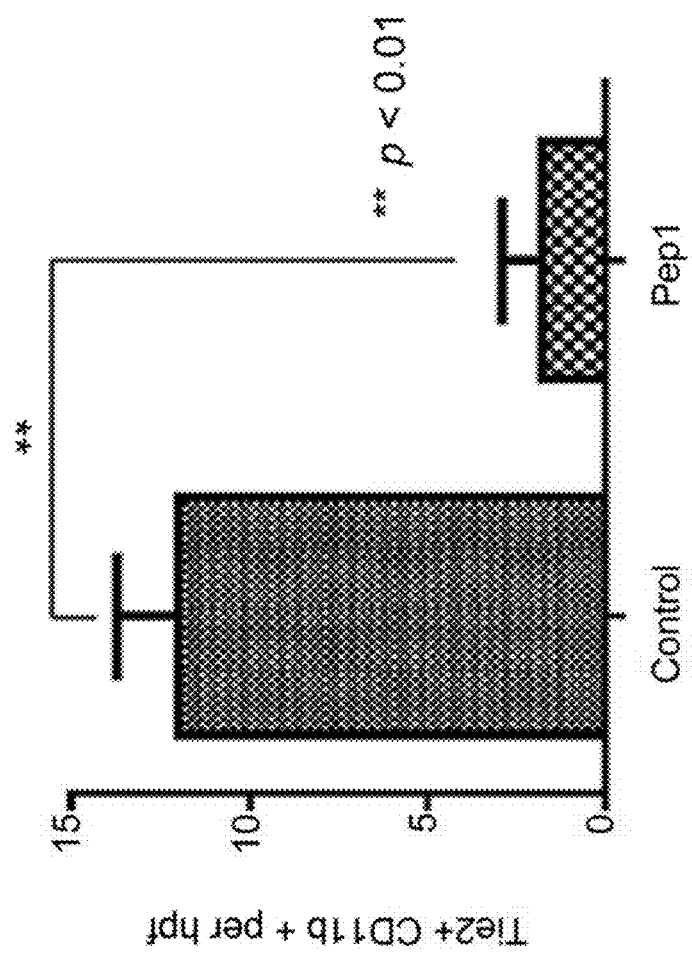

Tie2 plays a key role in the angiogenesis [Du R et al, Cancer cell, 13:206-20, 2008]. Based on that PEP1 can inhibit the expression of HIF-1α and VEGF by HSP destabilization, the experiment of whether PEP1 can recruit TEM (Tie2 expressing monocyte in tumor) was done. In the result of the immunohistochemical staining, it was confirmed that the number of Tie2+ CD11b+ monocytes collected from PEP1 treated mouse was significantly lower than that of the control mouse tumor (See FIGS. 12 and 13). It shows that the inhibition of the expression of HIF-1α and VEGF by PEP1 affects the recruitment TEM which is important to angiogenesis.

Example 7: Decreases of HSP70 and HSP90 in Tumors by PEP1 Treatment

Figure 14:
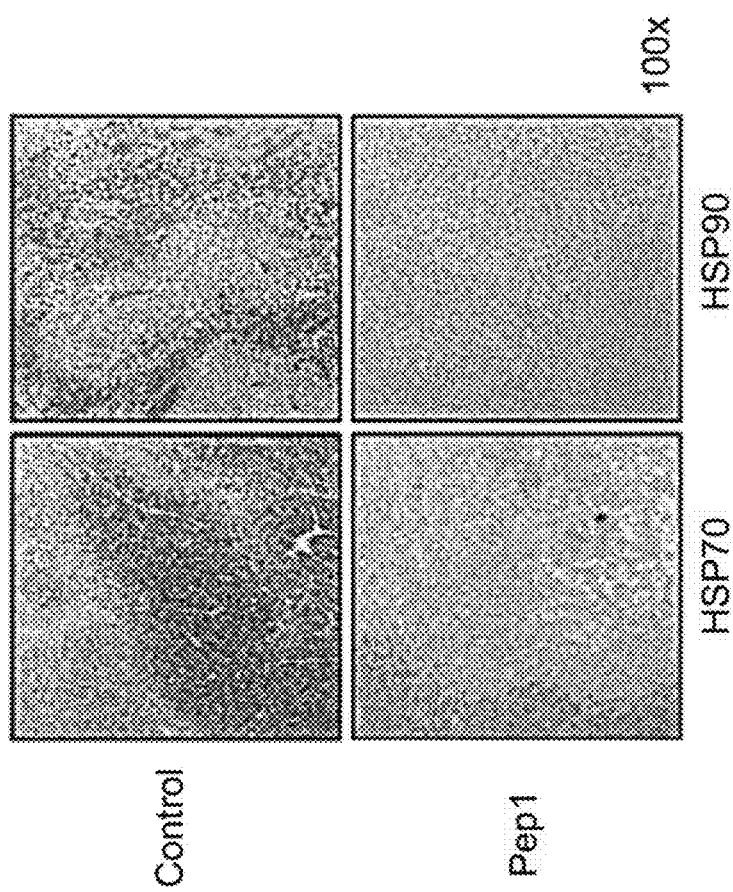
FIGS. 14 to 16 are the results which represent the decrease of HSP70 and HSP90 protein levels in tumor by treating PEP1. By using the immunohistochemical staining with the antibodies to HSP70 and HSP90, HSP70 and HSP90 protein levels were visualized (FIG. 14), and quantified by using Leica Qwin software (FIG. 15). The 10 fields were selected randomly for quantification from 6 slides of each treatment group (representation of data by mean±SD, versus control, *means $p<0.05$, using 2-way T-test). The protein extracts from tumor were immunoblotted by antibodies to HSP70, HSP90, GRP78, and GAPDH (FIG. 16).
Figure 15:
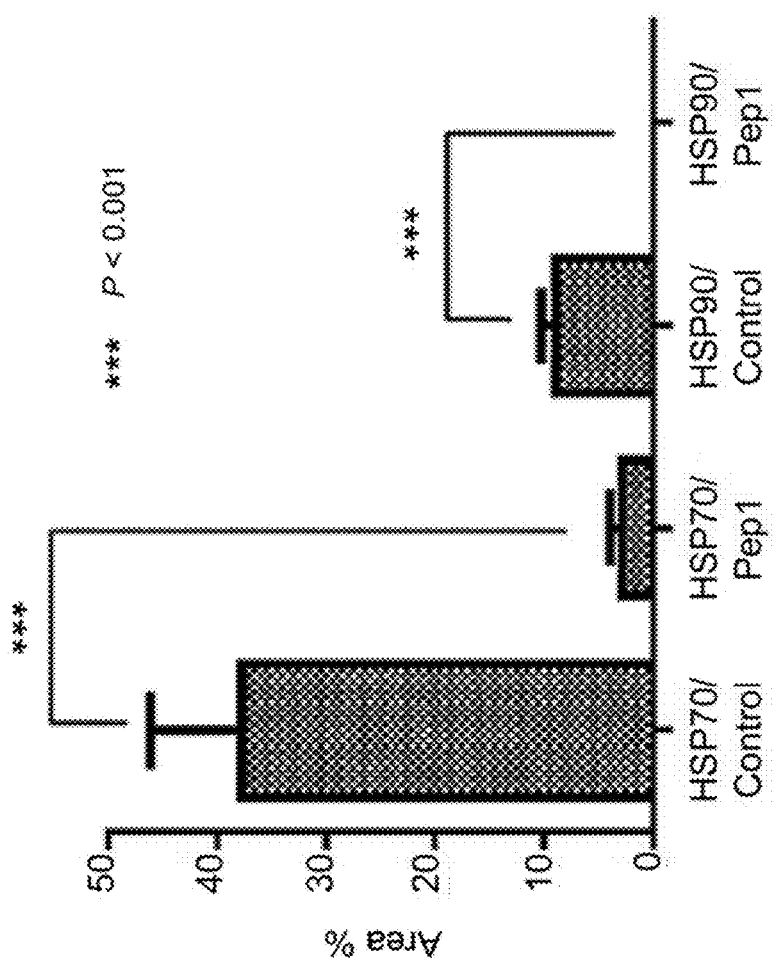

For verifying whether PEP1 inhibits the expressions of HSP70 and HSP90 in vivo, the immunohistochemical staining by the α-HSP70 or α-HSP90 antibodies was done. As consistent with the data from the cancer cell lines, the tumor section collected from PEP1 treated group, when compared to the PBS treated control group, showed weaker staining pattern (See FIG. 14). In PEP1 treated sample, the positive stained part was very small than that of the control group (See FIG. 15).

Figure 16:
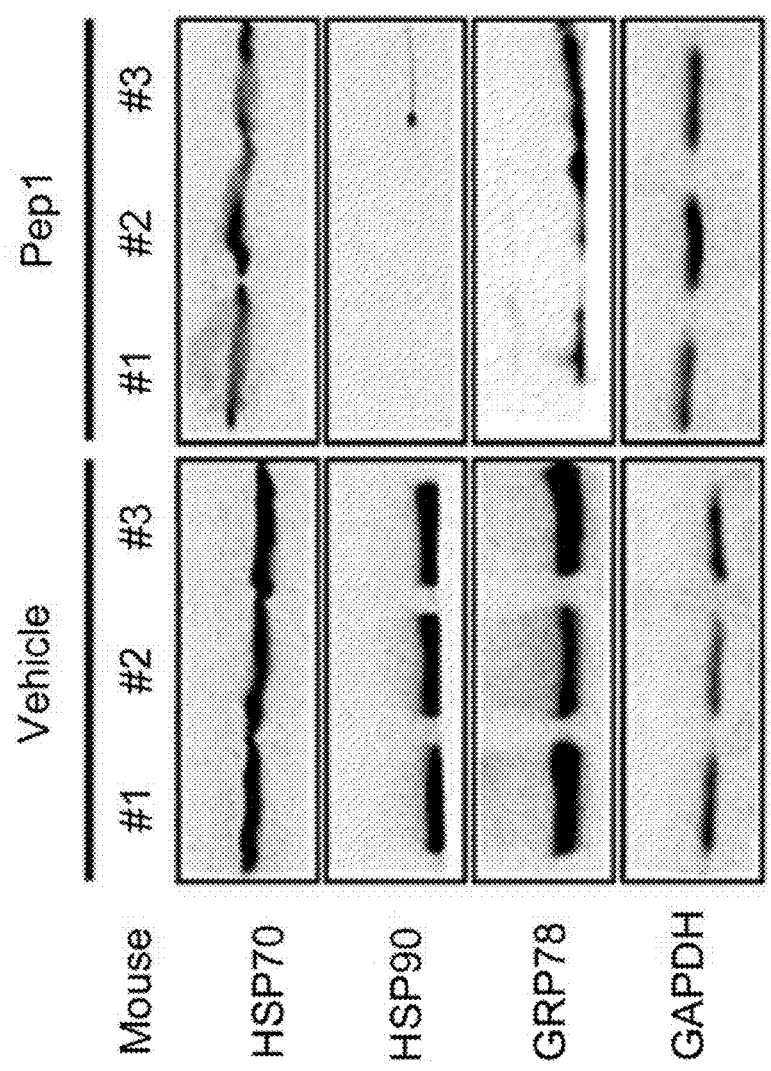

Decreases of HSP70 and HSP90 protein levels in PEP1 treated tumor sample were verified by immunoblotting experiment using tumor lysates. The decreases of HSP70 and HSP90 were observed in the all three PEP1 treated tumor samples (See FIG. 16). Especially HSP90 was scarcely found in the PEP1 treated sample. As the other family of HSP, GRP78 also decreased in the PEP1 treated sample. Synthetically these results prove that PEP1 decreases HSP in vivo system and has ability of inhibiting tumor growth.

Example 8: Effect of PEP1 to the Secreted HSP70 Level in Blood

Figure 17:
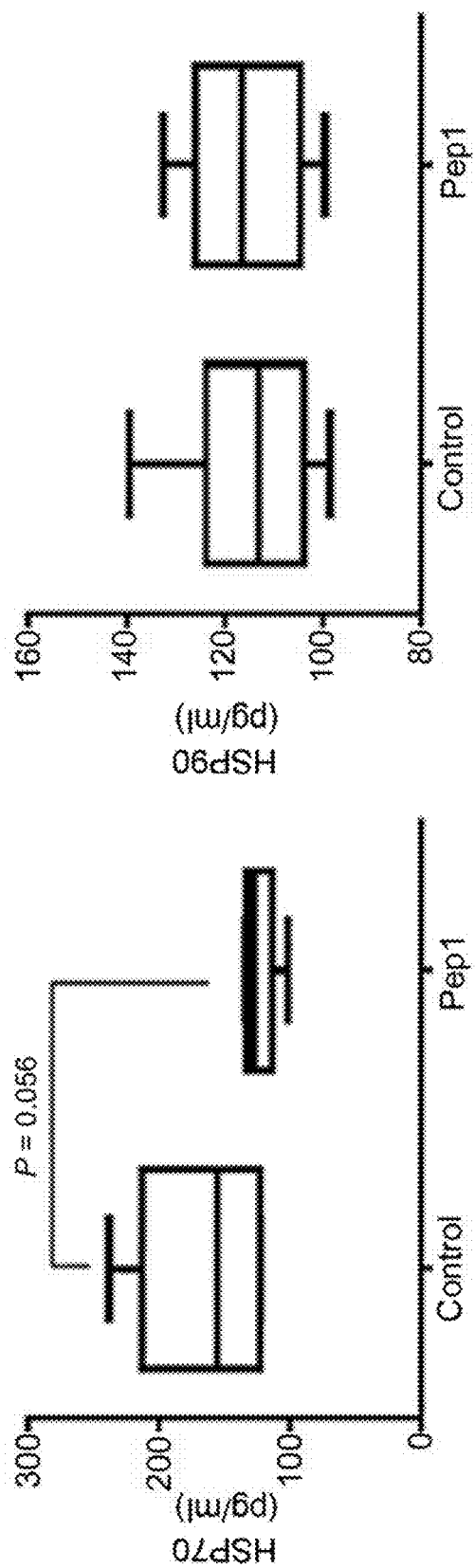
FIGS. 17 and 18 are the results which represent the effect of PEP1 to HSP70 secretion level in blood.

The HSP70 and HSP90 can be secreted from the tumor cells, and the recent researches have shown their several roles for tumor formation and anti-tumor reaction. In the secretion of HSP90 and HSP70, for explaining the role of PEP1 more detailed, the concentrations of HSP70 and HSP90 from the blood collected from the mouse having tumor were measured. Although there was no changes in the secreted HSP90 level between the PEP1 treated group and the control group, the HSP70 level of the PEP1 treated mouse was lower than that of the control group (See FIG. 17).

Figure 18:
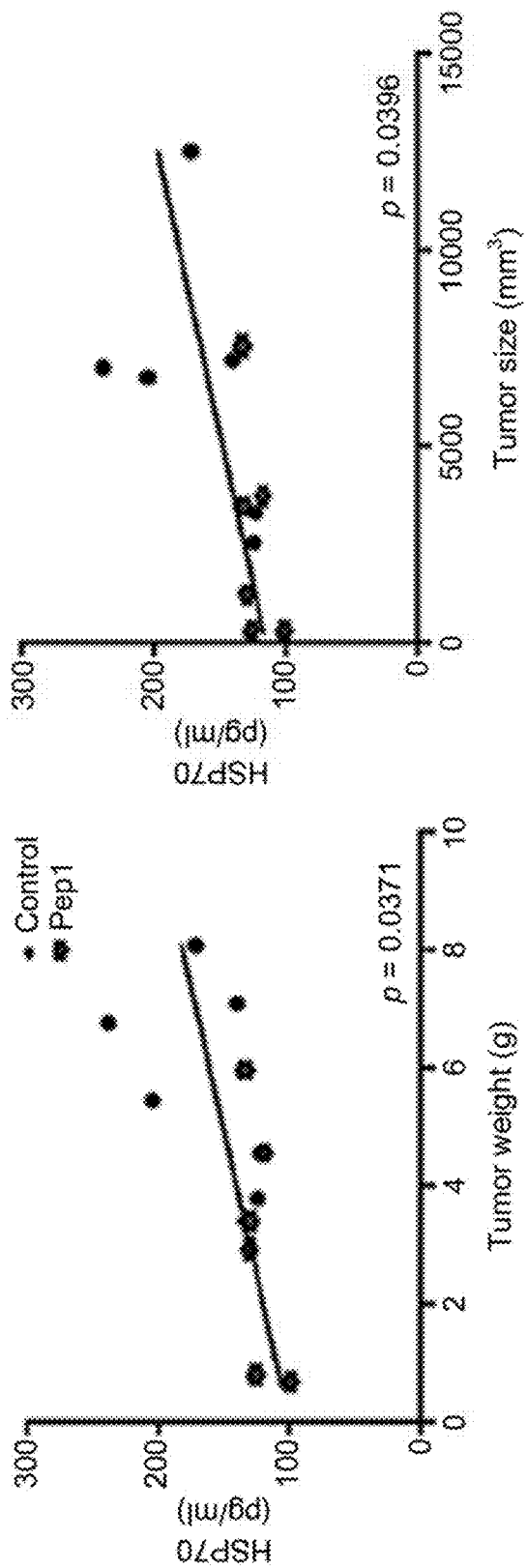

Also, the lower HSP70 level is related to the amount of tumor and the weight of tumor (See FIG. 18).

Example 9: Inhibition of the Tumor Growth by PEP1

The results of the above-mentioned examples show that the inhibition effect of PEP1 to the function of HSP90 and HSP70, and they suggest that PEP1 potentially has the tumor inhibiting effect like the other HSP inhibitors.

Figure 19:
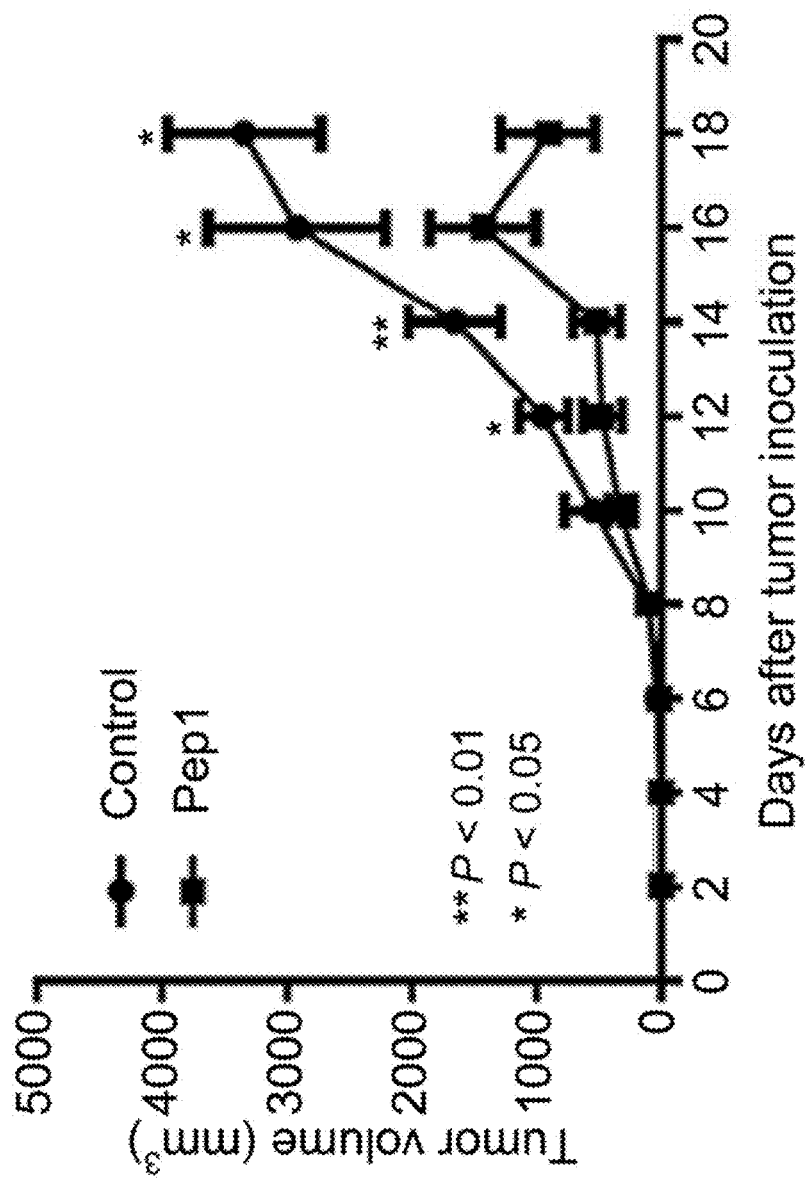
FIGS. 19 to 21 represents the inhibition of tumor growth in vivo by PEP1. MC38 cells are injected to BALB/c athymic (Nu/Nu) mouse (10 mice for 1 group; n=20) models subcutaneously. To the mouse model having tumor, PEP1 or PBS were injected intraperitoneally once every 2 days. When the diameter of tumor were 10 mm, PEP1 or PBS were injected into tumor. In the experiment of FIG. 19, the volume of tumor was measured every 2 days. In the experiment of FIG. 20, the weight of tumor was measured on 14 days after sacrificing the mouse. The eliminated tumor was shown in FIG. 21 (versus vehicle, *means $p<0.05$, **means $p<0.01$, using 2-way t-test).
Figure 20:
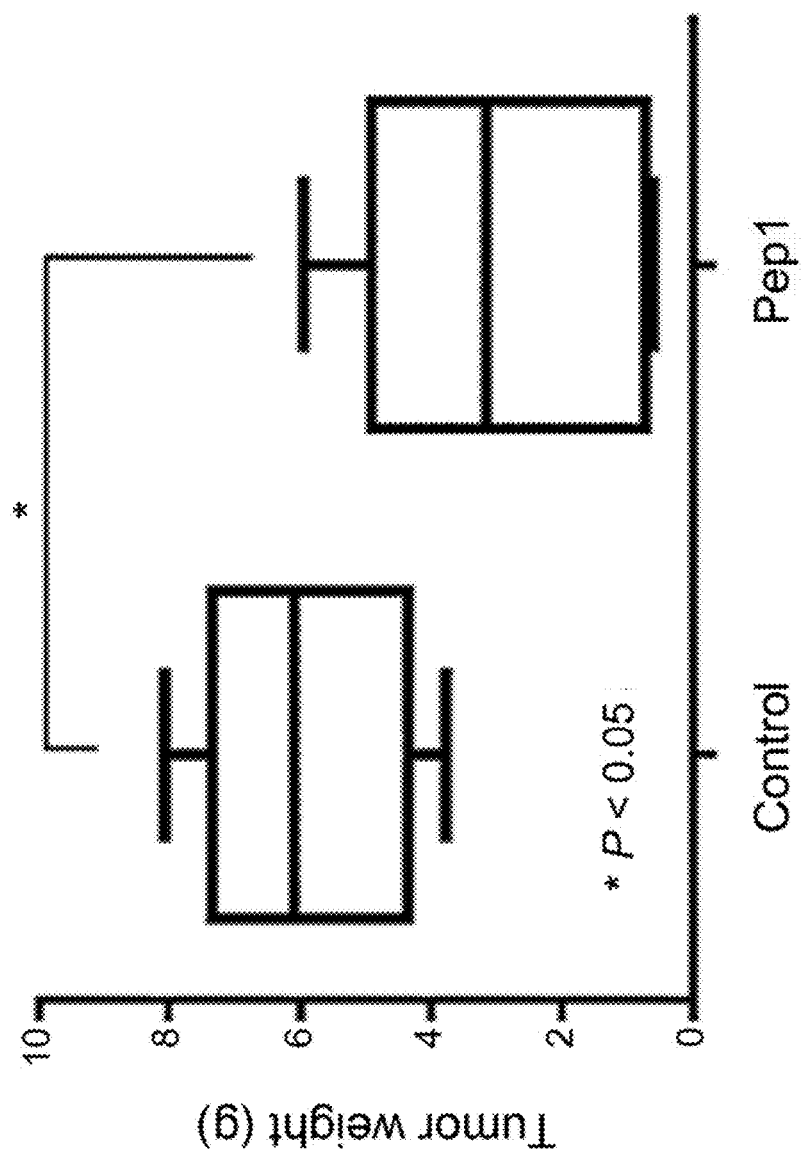
Figure 21:
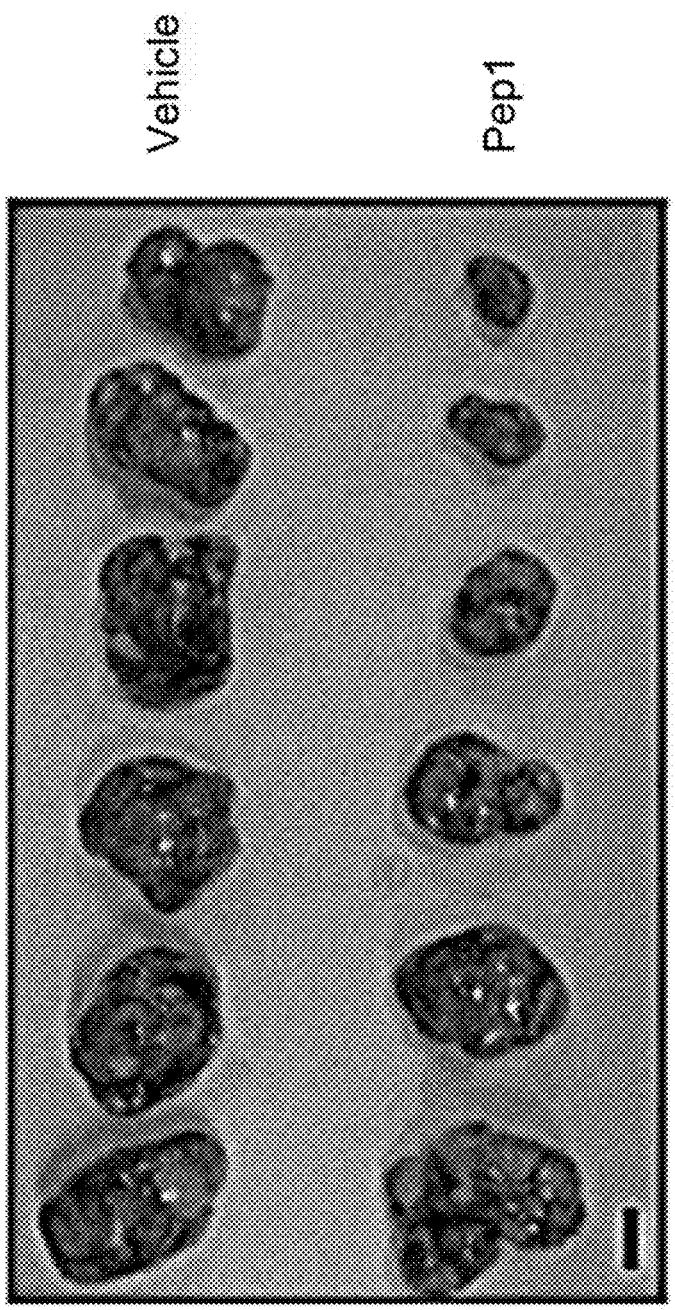

Therefore, in this example, it was studied that the tumor inhibiting effect of PEP1 in vivo by using the mouse model. The tumor growth in MC38 murine cancer cells with or without treating PEP1 was analyzed in vivo. The significant difference in the amount of tumor between PEP1 treated group and the control group was observed (See FIG. 19). At the time of the 18th day after injection, it was observed that the average amount of tumor of the control group was 3 times than that of PEP1 treated group. Synthetically, the tumor weight of the control group much heavier than that of the PEP1 treated group, and this result shows that PEP1 can inhibit the tumor growth in vivo (See FIGS. 20 and 21).

Figure 22:
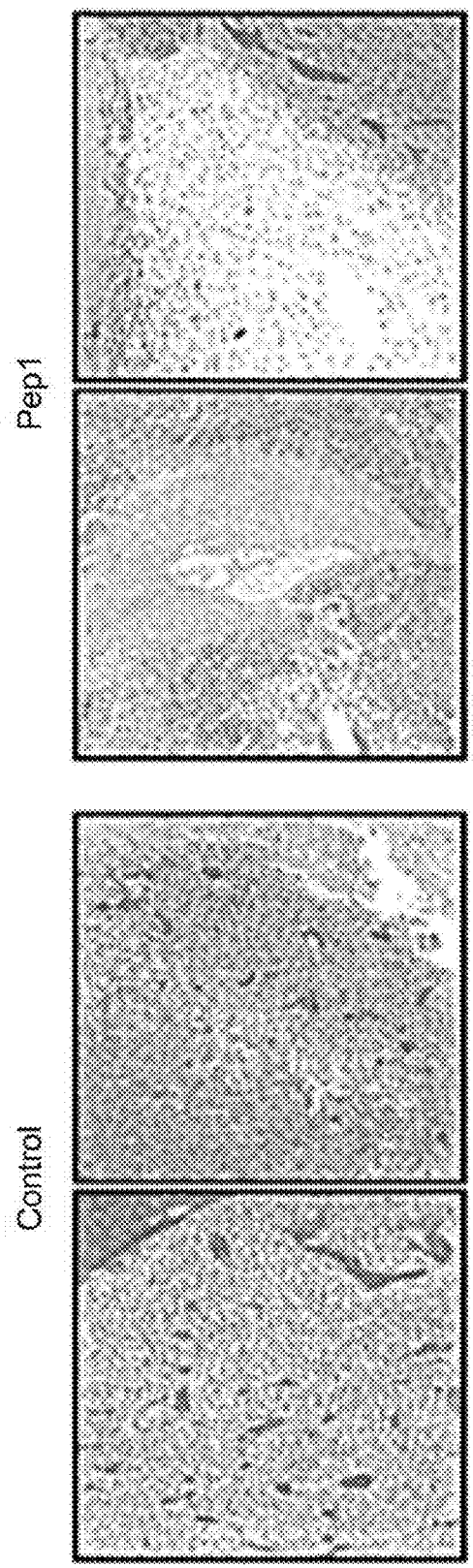
FIGS. 22 to 24 represent the results of histological test of the PEP1 administered mouse tumor. The tumor cells collected from the mouse model having tumor treated by PEP1 or vehicle were prepared for immunohistochemistry. In the experiment of FIG. 22, the paraffin fixed sections were stained by H&E staining, and observed by a microscope. In the experiment of FIG. 23, the apoptosis was analyzed by TUNEL assay with the sections. The experiment of the FIG. 24, the proliferating cells were analyzed by immunohistochemistry with PCNA (proliferating cell nuclear antigen) antibodies. The 10 fields were selected randomly from 6 slides of each treatment group, for the quantification, were analyzed by Leica Qwin software.
Figure 23:
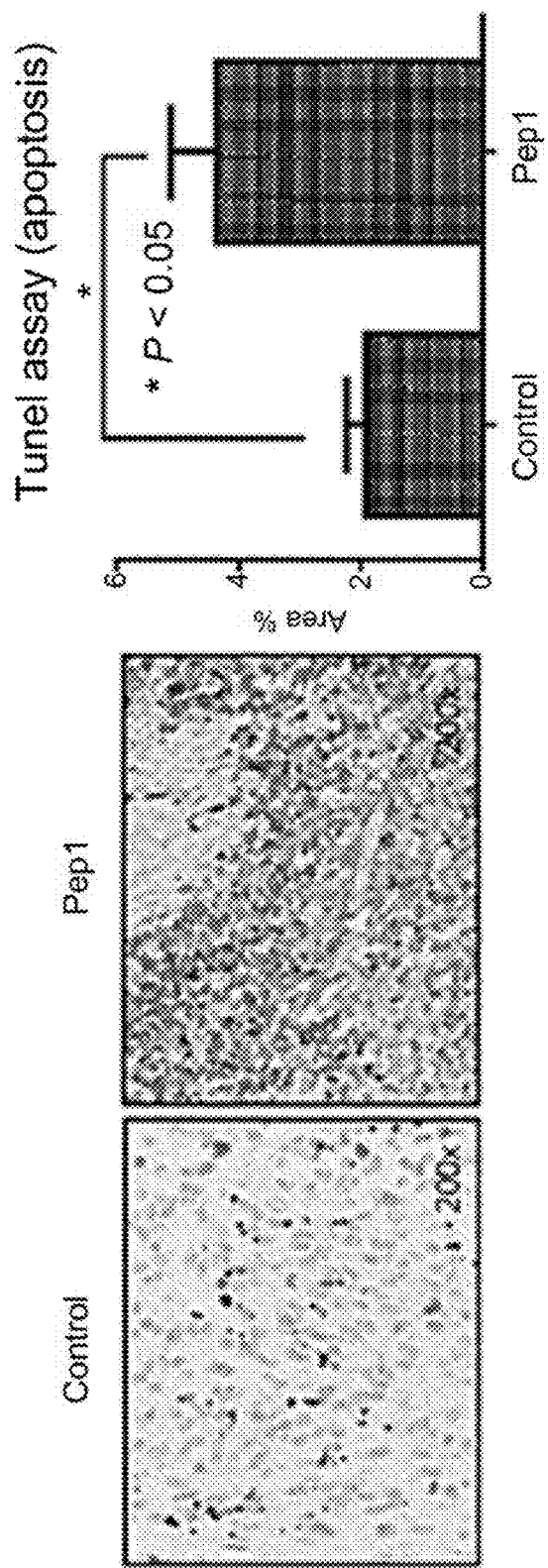
Figure 24:
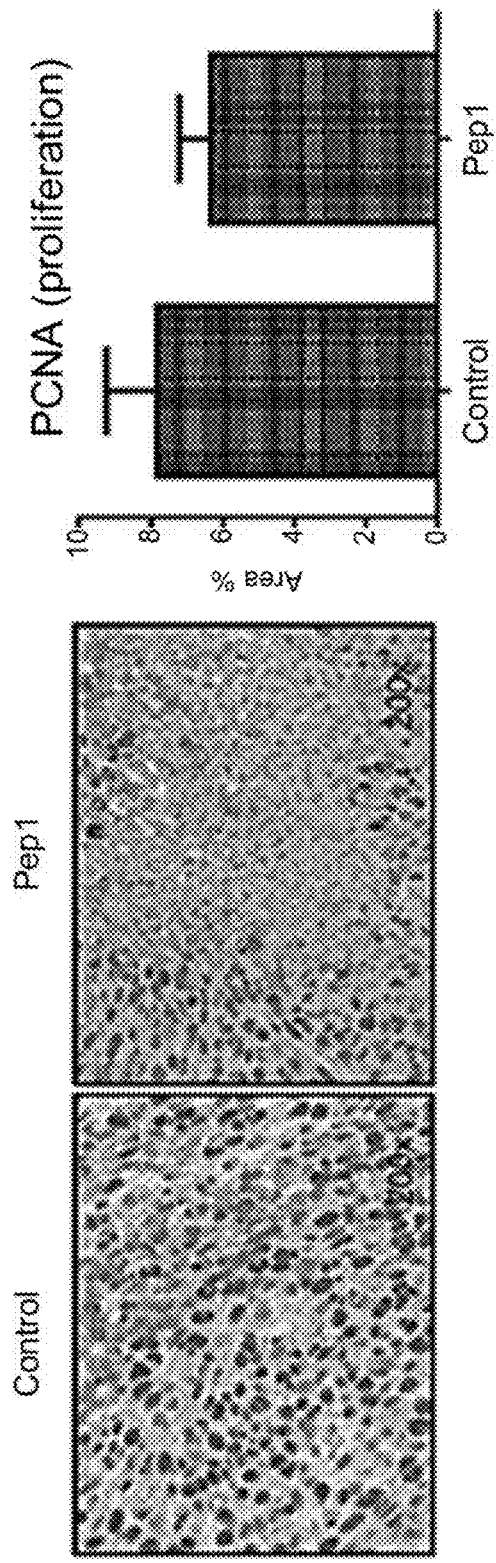
Figure 25A:
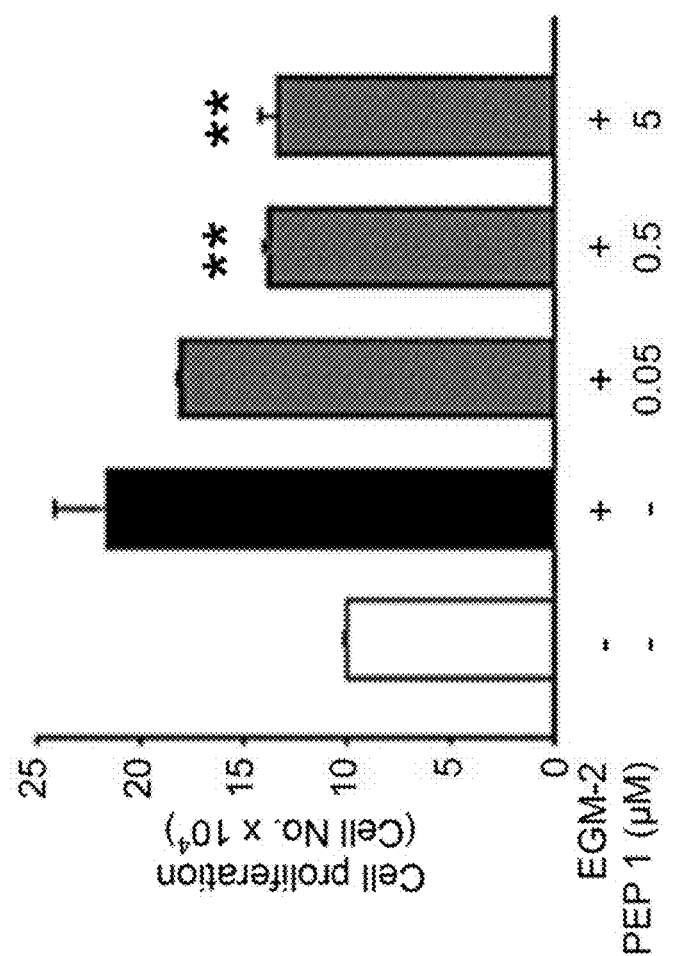
FIGS. 25a and 25b, as the experiments for the evaluation of the anti-angiogenesis effect of PEP1, in Human umbilical vein endothelial cells, after treating PEP1 at each concentration (0.05, 0.5, 5 μM), by measuring the cell proliferation (FIG. 1a) and the cell viability (FIG. 1b), represent the result of the inhibition effect of vascular endothelial cell proliferation.
Figure 25B:
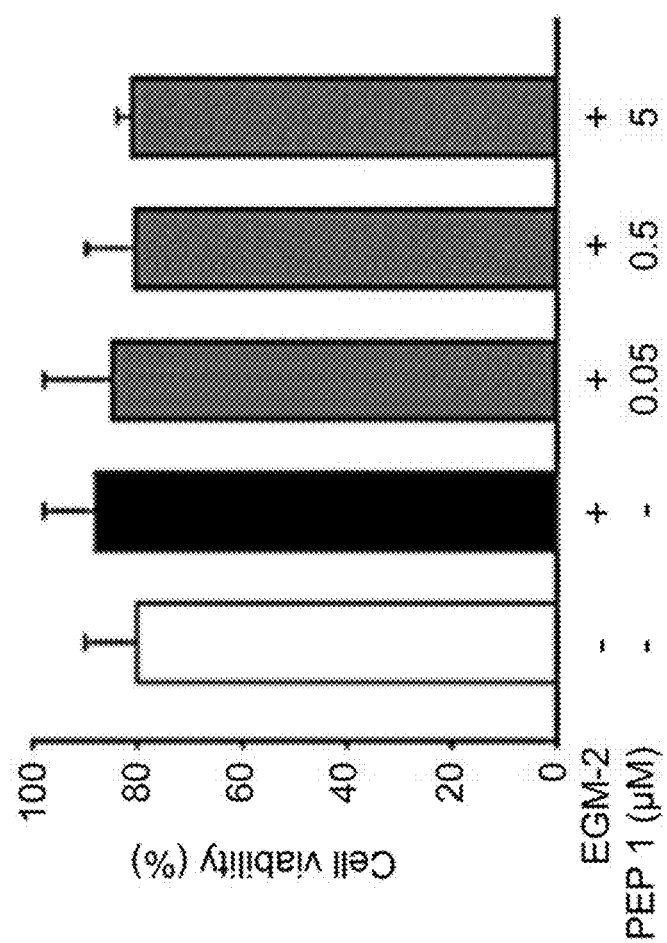
Figure 26A:
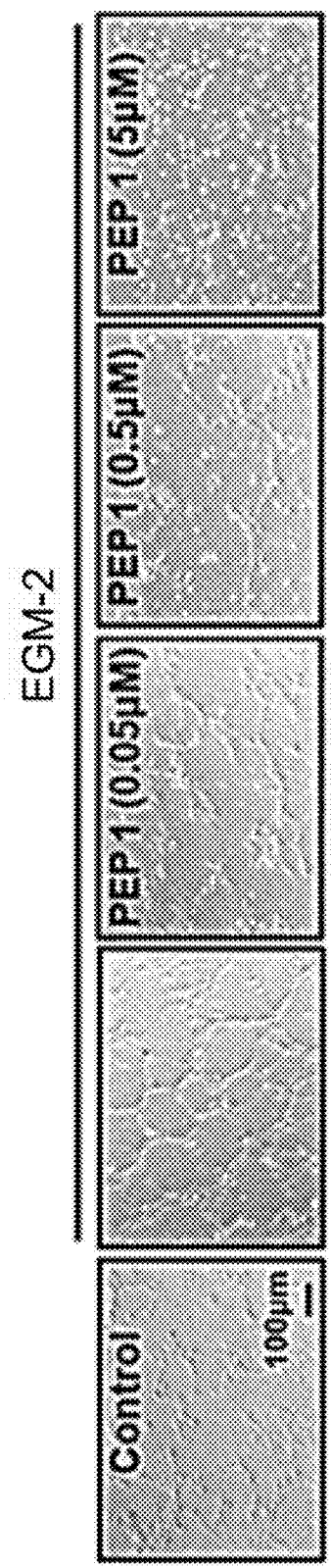
FIGS. 26a and 26b represent that, as the experiments for the evaluation of the anti-angiogenesis effect of PEP1, after treating PEP1 to the vascular endothelial cells at each concentration (0.05, 0.5, 5 μM), by observing the result (FIG. 2a) and making the graph (FIG. 2b), the effect of inhibiting vascularizing with vascular endothelial cell.
Figure 26B:
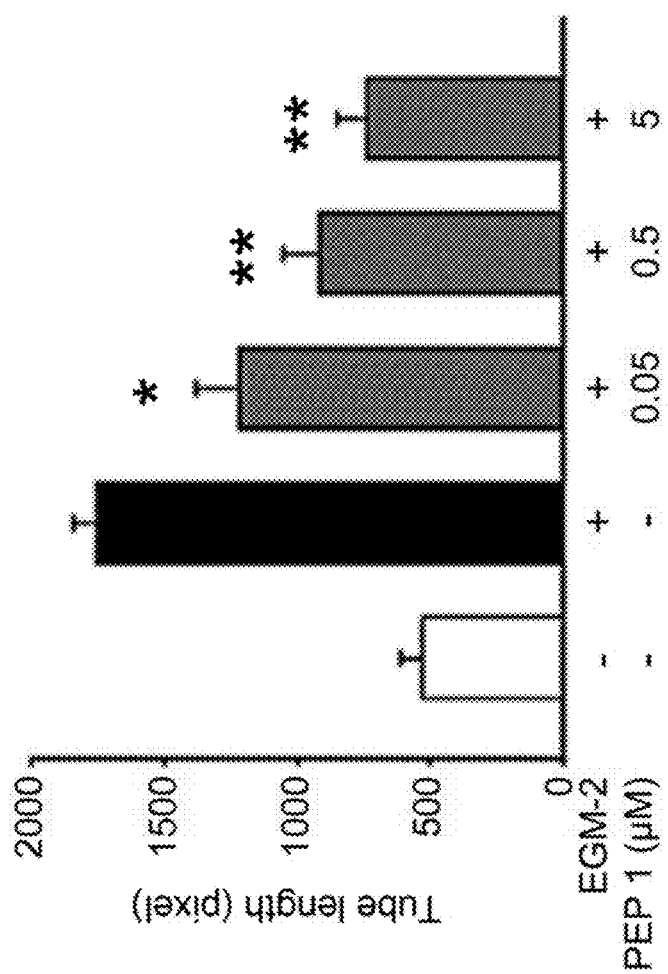
Figure 27A:
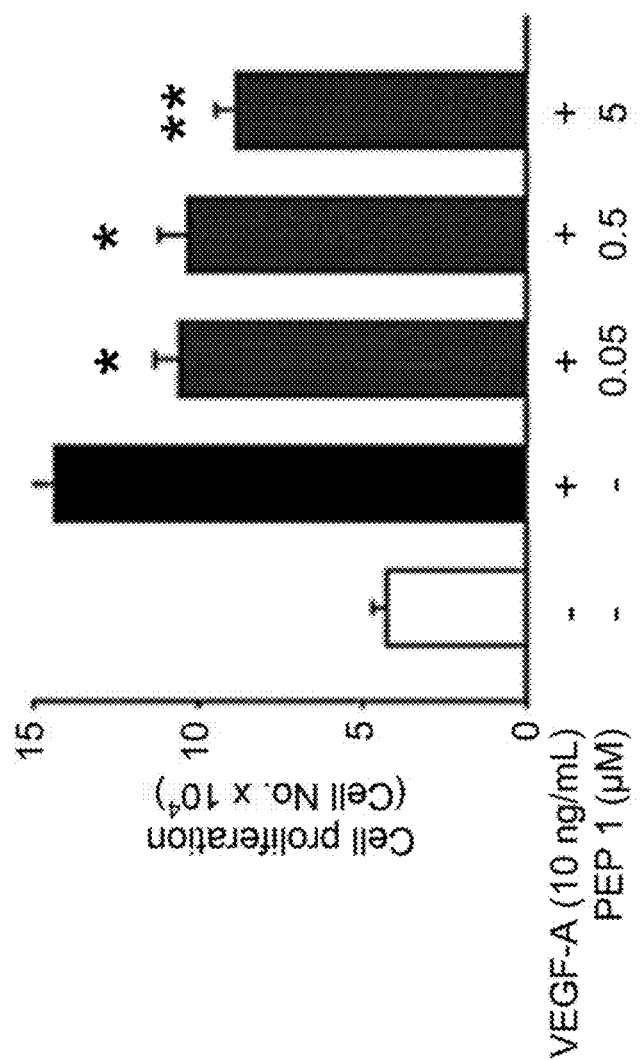
FIGS. 27a and 27b represent that, as the experiments for the evaluation of the anti-angiogenesis effect of PEP1, after treating PEP1 at each concentration (0.05, 0.5, 5 μM) to the vascular endothelial cells induced by VEGF-A (Vascular endothelial growth factor), by measuring the cell proliferation (FIG. 3a) and the cell viability (FIG. 3b), the result of observing the effect of inhibiting vascular endothelial cell proliferation.
Figure 27B:
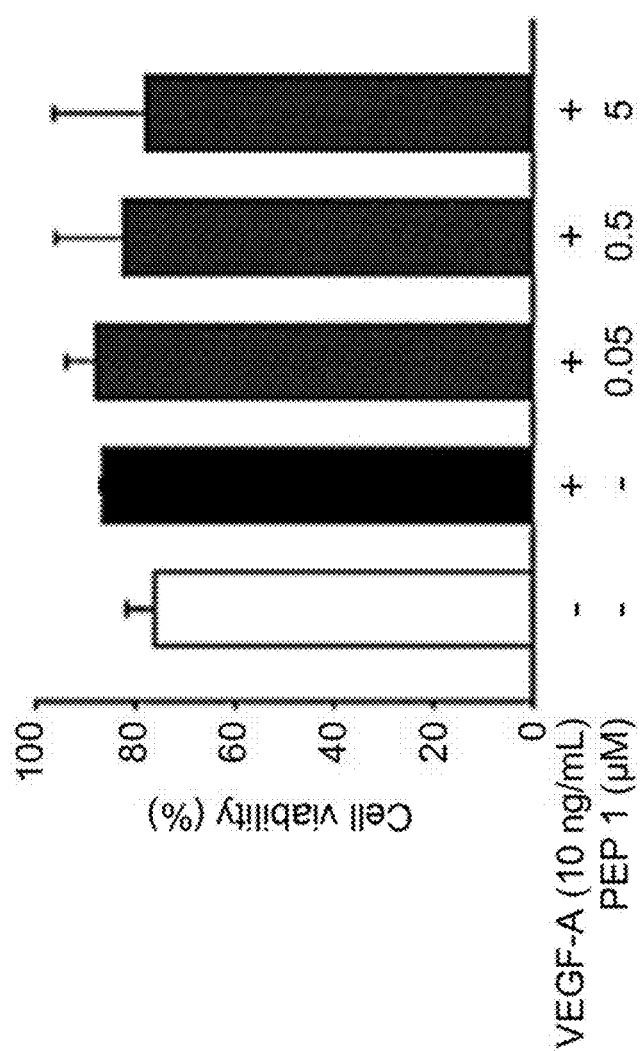
Figure 28A:
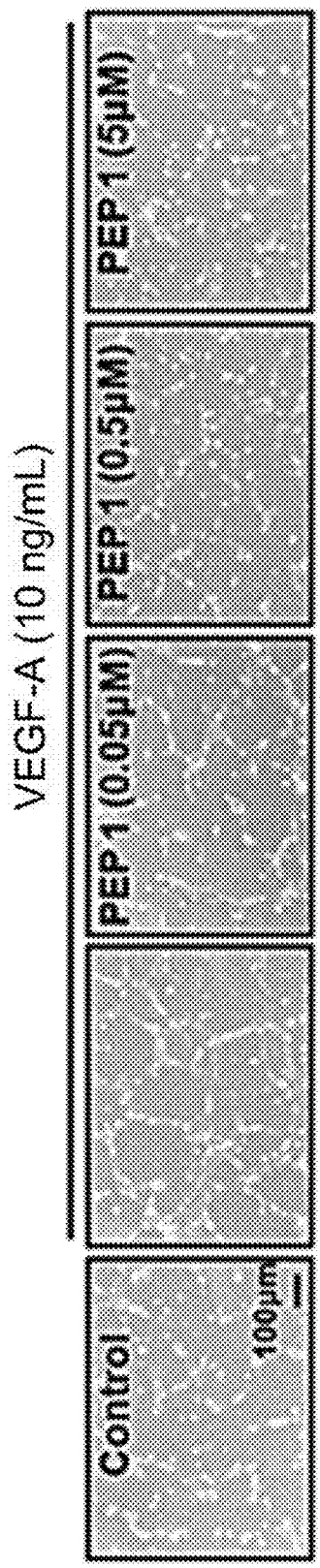
FIGS. 28a and 28b represent that, as the experiments for the evaluation of the anti-angiogenesis effect of PEP1, after treating PEP1 at each concentration (0.05, 0.5, 5 μM) to the vascular endothelial cells induced by VEGF-A (Vascular endothelial growth factor), by observing the result (FIG. 4a) and making the graph (FIG. 4b), the effect of inhibiting vascularizing with vascular endothelial cell.
Figure 28B:
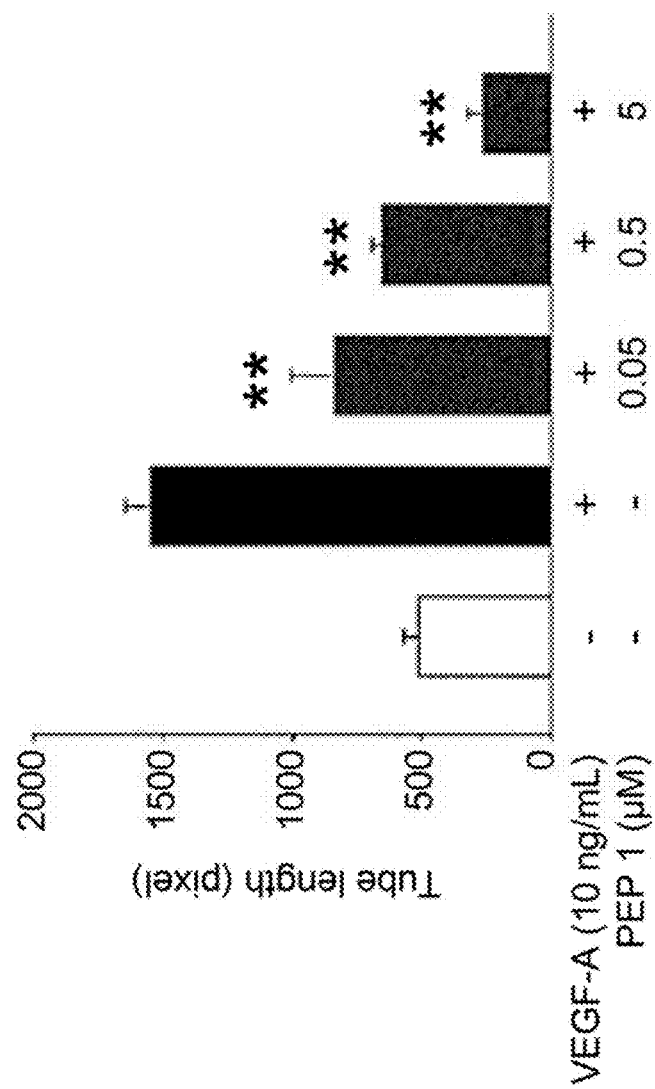
Figure 29:
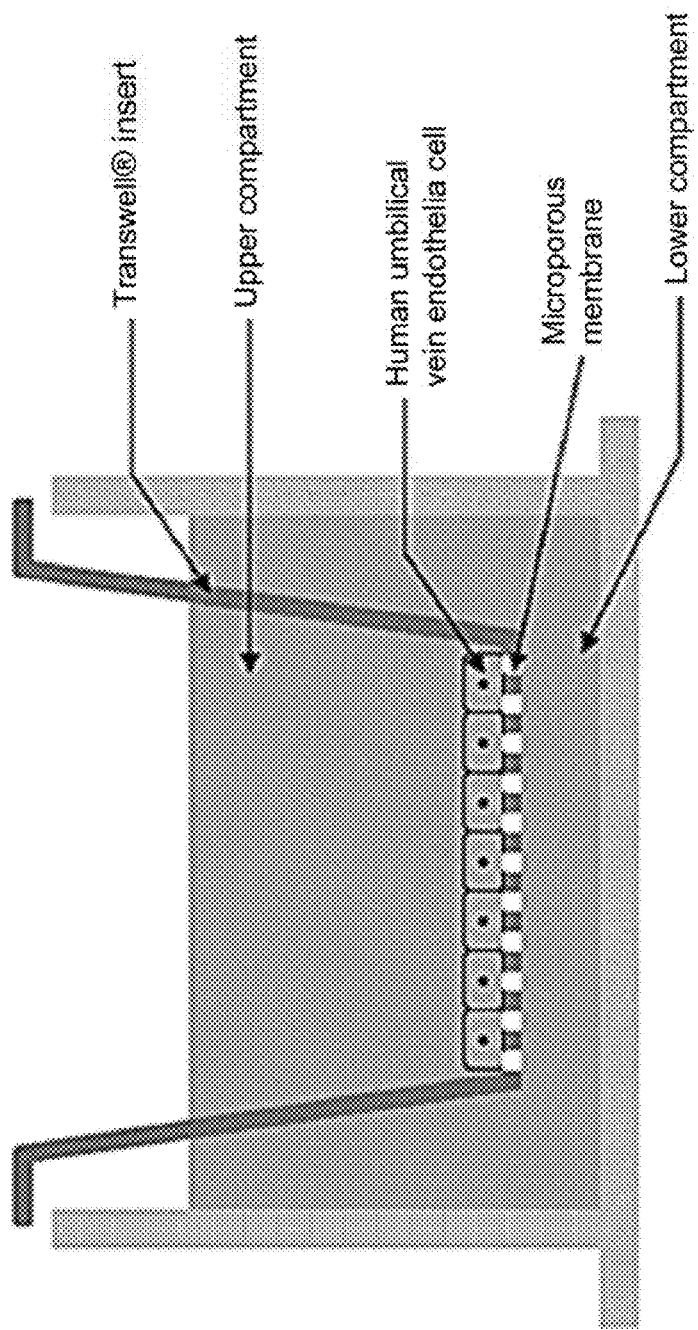
FIG. 29 is the sketch of mimetic diagram which is an installed Transwell insert.
Figure 30A:
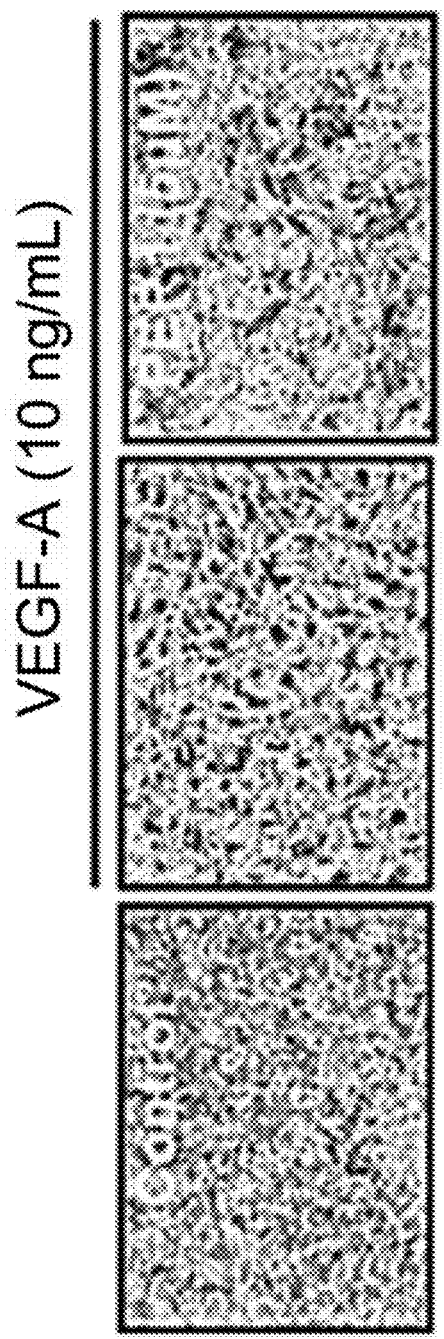
FIGS. 30a and 30b represent that, as the experiments for the evaluation of the anti-angiogenesis effect of PEP1, after treating PEP1 at each concentration (0.05, 0.5, 5 μM) to the vascular endothelial cells induced by VEGF-A (Vascular endothelial growth factor), by observing the result after fixing an insert by methanol and eliminating the non-invasion cells at the upper-part of the insert (FIG. 6a) and by making the graph (FIG. 6b), the result of inhibiting vascular endothelial cell invasion.
Figure 30B:
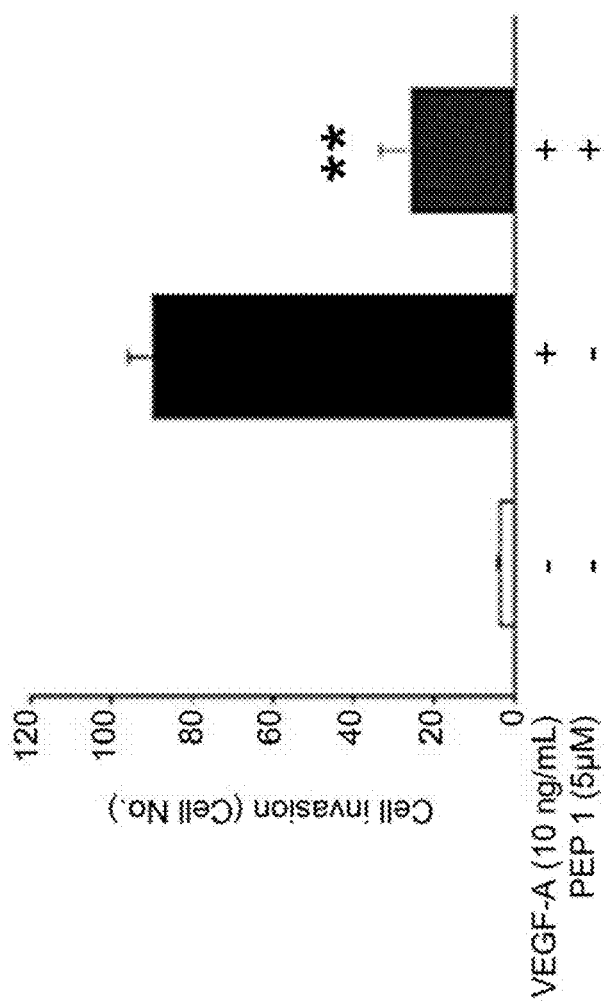

Example 10: Histological Test of the Tumor Collected from the PEP1 Treated Mouse The histological test by H&E (Hematoxylin and Eosin) staining shows that the tissue section of the PEP1 treated mouse has more cavities than that of the control group. It suggests that the more apoptosis occurred in the tumor of the PEP1 treated mouse (See FIG. 22). Also the less vascularization in the tumor collected from the PEP1 treated mouse was detected. It means that PEP1, as like as other HSP inhibitors, has the effect inhibiting angiogenesis (See FIG. 22). The progress of the cell apoptosis can be observed by TUNEL staining, and it surely confirms the anti-cancer effect of PEP1. As mentioned in FIG. 23, as compared with the tumor of the control group, the significant high level of the cell apoptosis in the PEP1 treated tumor sample was detected. Also, the tumor section staining for detecting the PCNA proliferation shows the decrease of the cell proliferation of the PEP1 treated group clearly (See FIG. 24).

Example 11: Verifying the Inhibition Effect of PEP1 to the Cell Proliferation and Angiogenesis in the Vascular Endothelial Cells 1) Cell Incubation In this example, the Human umbilical vein endothelial cell was incubated in the EGM-2 media and only the 2 to 5 cycles of the vascular endothelial cell was selected for the experiment.

2) Materials

As the experiment materials, the Human Umbilical vein endothelial cell (Lonza, Walkersville, Md., USA) and the VEGF-A (vascular endothelial growth factor-A Merck Millipore, Billerica, Mass., USA) were purchased respectively. PEP1 was solved in the PBS (phosphate-buffered saline, at pH 7.4) and used.

3) Analysis of the Proliferation of Vascular Endothelial Cells and its Effect

The vascular endothelial cells were plated to a 6-well plate (BD Biosciences, Bedford, Mass., USA) of the 1×105 cells/well. The cells were synchronized by the basic EBM-2 media (Lonza) which has no serum and angiogenesis factors, treated by PEP1 at each concentration (0.05, 0.5, 5 µM) and stimulated by the EGM-2 media, in order to observe the cell proliferation inhibition effect.

For detecting the cell proliferation, by using the trypan blue staining solution (Invitrogen, Carlsbad, Calif., USA), the cells were directly counted in the microscope (×100), and the cell viability was analyzed by using viability assay kit (Merck Millipore Inc.) with Muse™ analyzer.

PEP1 inhibited in a concentration-dependent way the vascular endothelial cells which were stimulated by the EGM-2 media including various angiogenesis inducers (FIG. 1a), and it did not affect the cell survival rate at all (FIG. 1b). It suggests that PEP1 effectively inhibits the vascular endothelial cell proliferation without cytotoxicity.

4) Analyzing the Endothelial Tube Formation of Vascular Endothelial Cell and the Effect On the 24-well plate coated by 200 µl of Matrigrl® basement membrane matrix (10.4 mg/mL, BD Biosciences) for 30 minutes at 37° C., the vascular endothelial cells were plated and serum-starved in the basic EBM-2 media for 2 hours. The change of the tube formation was observed by Olympus CKX41 inverted microscope (CAchN 10/0.25 php objective, Olympus Optical Co., Tokyo, Japan) and ToupTek Toupview software (version x86, 3.5.563, Hangzhou ToupTek Photonics Co., Zhejiang, P. R. China) (FIG. 2a).

It is suggested that PEP1 in a concentration-dependent way inhibits the tube formation of the vascular endothelial cell proliferation which was stimulated by the EGM-2 media including various angiogenesis inducers (FIG. 2b), and thereby being able to inhibit the angiogenesis by the movement and differentiation of the vascular endothelial cells.

Example 12: Verifying the Effect of PEP1 Inhibiting the Cell Proliferation, Angiogenesis, and Invasion of the Vascular Endothelial Cells by the VEGF-A 1) Analyzing the Proliferation and the Survival Rate by the VEGF-A in the Vascular Endothelia Cell and the Effect The vascular endothelial cells were plated to a 6-well plate (BD Biosciences, Bedford, Mass., USA) of the 1×105 cells/well. The cells were synchronized to the G1/G0 phase by the basic EBM-2 media (Lonza) which has no serum and angiogenesis factors, treated by the PEP1 at each concentration (0.05, 0.5, 5 µM) and stimulated by the VEGF-A (10 ng/mL) for 24 hours, in order to observe the cell proliferation inhibition effect.

For detecting the cell proliferation, by using the trypan blue staining solution (Invitrogen, Carlsbad, Calif., USA), the cells were directly counted in the microscope (×100), and the cell viability was analyzed by using viability assay kit (Merck Millipore Inc.) with Muse™ analyzer.

PEP1 in a concentration dependent way inhibited the vascular endothelial cell proliferation by VEGF-A similar to the condition of the EGM-2 including various angiogenesis inducers (FIG. 3a), but did not affect the cell survival rate (FIG. 3b).

2) Analyzing the Endothelial Tube Formation by VEGF-A and the Effect

On the 24-well plate coated by 200 µl of Matrigrl® basement membrane matrix (10.4 mg/mL, BD Biosciences) for 30 minutes at 37° C., the vascular endothelial cells (4×10$^4$ cells/well) were plated and serum-starved in the basic EBM-2 media for 2 hours. After treating with PEP1 at each concentration (0.05, 0.5, 5 µM) and the cells was stimulated by VEGF-A (10 ng/mL) for 6 hours. The change of the tube formation was observed by Olympus CKX41 inverted microscope (CAchN 10/0.25 php objective, Olympus Optical Co., Tokyo, Japan) and ToupTek Toupview software (version x86, 3.5.563, Hangzhou ToupTek Photonics Co., Zhejiang, P. R. China) (FIG. 4a).

It was verified that PEP1 in a concentration dependent way inhibits the endothelial tube formation by VEGF-A in the vascular endothelial cell (FIG. 4b).

3) Analyzing the Invasion of the Vascular Endothelial Cell by VEGF-A and its Effect The vascular endothelial cells of the serum-starvation by the basic EBM-2 media for 2 hours were plated each as 100 mL (4×10$^5$ cells/mL) to Matrigel® (1 mg/mL, BD Biosciences)-coated transwell insert (Costar, 6.5 mm diameter), and the 600 µl basic EBM-2 media was added to the under well. The mimetic diagram of the installed insert was shown in the FIG. 5.

After treating with PEP1 at each concentration (0.05, 0.5, 5 µM) and stimulating by VEGF-A (10 ng/mL) for 18 hours, the insert was fixed by the methanol and the non-infiltrated cells in the upper side of the insert was eliminated by using cotton-tipped swab. After staining by the Giemsa stain solution (Sigma-Aldrich Co., St. Louis, Mo., USA) and observing the 6 different parts by the microscope (×200), the infiltrated cells were directly counted by using the microscope (FIG. 6a).

It was verified that PEP1 strongly inhibits the cell invasion by the VEGF-A (FIG. 6b).

The statistical significance of the experiment results was analyzed by the student's t test, and the p-value was defined as the statistically significant value when it is lower than 0.05.

---

What is claimed is:

1. A method for treating an angiogenesis-related disease comprising administering to a subject in need thereof the isolated peptide of SEQ ID NO: 1, wherein the angiogenesis-related disease is selected from a group consisting of metastasis, diabetic retinopathy, retinopathy of prematurity, corneal graft rejection, neovascular glaucoma, scarlet syndrome, proliferative retinopathy, psoriasis, macular degeneration, hemophilic arthropathy, capillary proliferation within atherosclerotic plaques, keloid, wound granulation, vascular adhesion, rheumatoid arthritis, chronic inflammation, osteoarthritis, autoimmune disease, Crohn's disease, restenosis, atherosclerosis, stenosis of intestine, cat scratch disease, ulcers, cirrhosis complications, glomerulonephritis, diabetic nephropathy, malignant nephrosclerosis, thrombotic micro vascular syndrome, organ transplant rejection, glomerulopathy, diabetes, uncontrolled angiogenesis-related disorders, diseases of inflammation and neurodegeneration.

2. The method according to claim 1, wherein the peptide is administered in a single dose at a concentration of 10 ng/kg to 10 mg/kg.

3. The method according to claim 1, wherein the peptide is administered 1 to 3 times a day.

4. The method of claim 1, wherein the peptide is administered at a daily dose of 10 ng/kg to 10 mg/kg.

5. A method for treating an angiogenesis-related disease comprising administering to a subject in need thereof a composition comprising the isolated peptide of SEQ ID NO:1, wherein the angiogenesis-related disease is selected from a group consisting of metastasis, diabetic retinopathy, retinopathy of prematurity, corneal graft rejection, neovascular glaucoma, scarlet syndrome, proliferative retinopathy, psoriasis, macular degeneration, hemophilic arthropathy, capillary proliferation within atherosclerotic plaques, keloid, wound granulation, vascular adhesion, rheumatoid arthritis, chronic inflammation, osteoarthritis, autoimmune disease, Crohn's disease, restenosis, atherosclerosis, stenosis of intestine, cat scratch disease, ulcers, cirrhosis complications, glomerulonephritis, diabetic nephropathy, malignant nephrosclerosis, thrombotic micro vascular syndrome, organ transplant rejection, glomerulopathy, diabetes, uncontrolled angiogenesis-related disorders, diseases of inflammation and neurodegeneration.

6. The method according to claim 5, wherein the angiogenesis-related disease is metastasis.

7. The method according to claim 5, wherein the composition is a pharmaceutical composition.

8. The method according to claim 5, wherein the composition is a food composition.

9. The method of claim 5, wherein the composition is administered through oral, rectal, transdermal, intravenous, intramuscular, intraperitoneal, in the bone marrow, epidural, or subcutaneous routes.

10. The method of claim 5, wherein the composition comprises 0.01 g/L to 1 kg/L of the isolated peptide.

11. The method of claim 5, wherein the peptide is administered in a single dose at a concentration of 10 ng/kg to 10 mg/kg.

12. The method of claim 5, wherein the peptide is administered 1 to 3 times a day.

13. The method of claim 5, wherein the peptide is administered at a daily dose of 10 ng/kg to 10 mg/kg.

14. The method according to claim 5, wherein the method inhibits proliferation of vascular endothelial cells, VEGF (Vascular endothelial growth factor)-induced tube formation and invasion of vascular endothelial cells.

15. The method according to claim 5, wherein the composition inhibits proliferation of vascular endothelial cells or tube formation.

16. The method according to claim 5, wherein the composition inhibits the proliferation of vascular endothelial cells by VEGF-A (Vascular endothelial growth factor-A), the tube formation, or the invasion of vascular endothelial cell.

* * * * *